United States Patent
Cheng et al.

(10) Patent No.: US 9,109,087 B2
(45) Date of Patent: Aug. 18, 2015

(54) LOW MOLECULAR WEIGHT BRANCHED POLYAMINES FOR DELIVERY OF BIOLOGICALLY ACTIVE MATERIALS

(75) Inventors: Wei Cheng, Singapore (SG); Daniel J. Coady, San Jose, CA (US); Amanda C. Engler, San Jose, CA (US); James L. Hedrick, Pleasanton, CA (US); Pei Yun Teo, Singapore (SG); Chuan Yang, Singapore (SG); Yi Yan Yang, Singapre (SG)

(73) Assignees: International Business Machines Corporation, Armonk, NY (US); Agency For Science, Technology And Research, Singapore (SG)

( * ) Notice: Subject to any disclaimer, the term of this patent is extended or adjusted under 35 U.S.C. 154(b) by 464 days.

(21) Appl. No.: 13/613,353

(22) Filed: Sep. 13, 2012

(65) Prior Publication Data

US 2014/0073048 A1    Mar. 13, 2014

(51) Int. Cl.
*A61K 47/30*    (2006.01)
*C07D 321/00*   (2006.01)
*C07H 21/00*    (2006.01)
*C08G 73/02*    (2006.01)

(52) U.S. Cl.
CPC ................ *C08G 73/0206* (2013.01)

(58) Field of Classification Search
CPC ....... A61K 47/30; C07D 321/00; C07H 21/00
USPC .......... 424/486; 514/772; 536/23.1; 549/228
See application file for complete search history.

(56) References Cited

U.S. PATENT DOCUMENTS

| | | | |
|---|---|---|---|
| 6,696,038 B1 | 2/2004 | Mahato et al. | |
| 2005/0059068 A1 | 3/2005 | Huang et al. | |
| 2007/0231392 A1 | 10/2007 | Wagner et al. | |
| 2009/0233359 A1* | 9/2009 | Kwon | 435/375 |
| 2010/0075420 A1 | 3/2010 | Saraf et al. | |
| 2010/0305281 A1* | 12/2010 | Fujiwara et al. | 525/461 |
| 2011/0182996 A1 | 7/2011 | Fukushima et al. | |

FOREIGN PATENT DOCUMENTS

| | | |
|---|---|---|
| CN | 101575416 A | 11/2009 |
| CN | 101638484 A | 2/2010 |
| EP | 2172508 A1 | 4/2010 |
| EP | 1320386 B1 | 3/2011 |

OTHER PUBLICATIONS

Pasquier et al, Biomacromolecules 8:2874-2882, 2007.*
Pasquier et al, Macromol. Biosci. 8:903-915, 2008.*
He et al, Macromolecular Chem. and Phys. 211: 2366-2381, 2010.*
Luo et al, Biomaterials 32:9925-9939, 2011; avail. online Sep. 17, 2011.*
Doody, et al., "Characterizing the structure/function parameter space of hydrocarbon-conjugated branched polyethylenimine for DNA delivery in vitro," Journal of Controlled Release, 2006, 16, 227-237, Jul. 25, 2006.
Gabrielson, et al., "Efficient polyethylenimine-mediated gene delivery proceeds via a caveolar pathway in HeLa cells," Journal of Controlled Release 136 (2009) 54-61, Available online Feb. 13, 2009.
Goel, V., Thesis titled "Quat-Primer" polymers based on b-PEI and their application in composites, Aachen University, Germany, Jan. 26, 2010.
Griffiths, et al., "Derivatizing weak polyelectrolytes—Solution properties, self-aggregation, and association with anionic surfaces of hydrophobically modified poly(ethylene imine)," Journal of Colloid and Interface Science 314 (2007) 460-469; Available online Jun. 7, 2007.
Guo, et al., "Receptor-Targeted Gene Delivery ViaFolate—Conjugated Polyethyleninnine," AAPS Pharmsci 1999; 1 (4); Published: Dec. 10, 1999.
Gusachenko, et al., "PEI—Cholesterol Conjugates with Different Levels of Modification" Journal of Biomaterials Science, Polymer Edition, 2009, 20:7-8, 1091-1110.
Huang, et al., "Inhibition of Bcl-2 expression by a novel tumor-specific RNA interference system increases chemosensitivity to 5-fluorouracil in Hela cells," Acta Pharmacologica Sinica Feb. 2006; 27 (2): 242-248.
Livak, et al., "Analysis of Relative Gene Expression Data Using Real-Time Quantitative PCR and the 2-ΔΔCT Method", Methods 25, 402-408 (2001).
Pasquier, et al., "Amphiphilic Branched Polymers as Antimicrobial Agents," Macromol. Biosci. 2008, 8, 903-915;published online: Sep. 10, 2008.
Pasquier, et al., "From Multifunctionalized Poly(ethylene imine)s toward Antimicrobial Coatings," Biomacromolecules, 2007, 8 (9), 2874-2882; Published on Web Aug. 3, 2007.
Pratt, et al., "Tagging alcohols with cyclic carbonate: a versatile equivalent of (meth)acrylate for ring-opening polymerization", ChemComm 2008, 114-116. First published on web Oct. 25, 2007.

(Continued)

*Primary Examiner* — Kevin Hill
(74) *Attorney, Agent, or Firm* — Michael R. Roberts

(57) ABSTRACT

A branched polyamine comprises about 8 to about 12 backbone tertiary amine groups, about 18 to about 24 backbone secondary amine groups, a positive number n' greater than 0 of backbone terminating primary amine groups, and a positive number q greater than 0 of backbone terminating carbamate groups of formula (2):

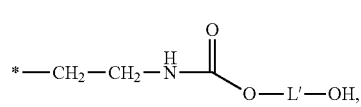

(2)

wherein (n'+q) is a number equal to about 8 to about 12, the starred bond of formula (2) is linked to a backbone nitrogen of the branched polyamine, L' is a divalent linking group comprising 3 to 30 carbons, and q/(n'+q)×100% equals about 9% to about 40%.

22 Claims, 15 Drawing Sheets

(56) References Cited

OTHER PUBLICATIONS

Yang, et al., "The role of non-covalent interactions in anticancer drug loading and kinetic stability of polymeric micelles," Biomaterials 33 (2012) 2971-2979; Available online Jan. 13, 2012.

Zanta, et al., "In Vitro Gene Delivery to Hepatocytes with Galactosylated Polyethylenimine," Bioconjugate Chem. 1997, 8, 839-844; published Oct. 1, 1997.

Zhao, et al., "Starburst low-molecular weight polyethylenimine for efficient gene delivery," J Biomed Mater Res Part A 2012:100A:134-140; Published online Oct. 14, 2011.

Zintchenko, et al., "Simple Modifications of Branched PEI Lead to Highly Efficient siRNA Carriers with Low Toxicity," Bioconjugate Chem. 2008, 19, 1448-1455; published on web Jun. 14, 2008.

Korean Intellectual Property Office, International Search Report and Written Opinion for PCT/US2013/057978, mailed Oct. 23, 2013.

* cited by examiner

LOW MOLECULAR WEIGHT BRANCHED POLYAMINES FOR DELIVERY OF BIOLOGICALLY ACTIVE MATERIALS

PARTIES TO A JOINT RESEARCH AGREEMENT

This invention was made under a joint research agreement between International Business Machines Corporation and the Agency For Science, Technology and Research.

BACKGROUND

The invention relates to low molecular weight branched polyamines for delivery of biologically active materials, and more specifically, to carbamate functionalized low molecular weight branched polyethylenimines comprising hydrophobic carbamate end groups for gene delivery.

Nucleic acid-based therapy holds great promise in treating human diseases. In principle, not only can faulty and defective genes be corrected and replaced by functional ones, but redundant gene expression could also be repressed to normal level by the use of RNA interference. In general, there are two major types of gene delivery vectors, viral and non-viral vectors. Although viral vectors have superior transduction capabilities, the immunogenic and oncogenic potential of viral vectors limits their clinical applications. To circumvent this problem, a number of non-viral gene delivery systems have been reported, which include (1) complex of nucleic acids with various cationic molecules including lipids, polymers and peptides and (2) conjugation of nucleic acids with natural ligands such as, for example, cholesterol and cell penetration peptide. Non-viral gene delivery vectors are receiving increasing attention due to biosafety, low production cost, ease of transportation and storage, reproducibility, and tunable functionalities for targeting specific cell types.

Among the various types of non-viral vectors branched polyethylenimine (weight average molecular weight (Mw) of 25 kDa, number average molecular weight (Mn) of 10 kDa, referred to herein as bPEI-25), which contains primary, secondary and tertiary amine groups, provides high gene transfection efficiency in vitro, and is regarded as an industry standard. bPEI-25 has a high cationic charge density at physiological pH, where about 20% of amine groups (i.e., primary amines) in bPEI-25 are protonated. This allows bPEI-25 to interact electrostatically with negative charged nucleic acids over a broad pH range and to complex them into nanoparticles. Once bPEI-25/nucleic acid nanocomplexes are internalized by the cells, the secondary and tertiary amines facilitate the release of the nucleic acids from the endosomes through the "proton sponge effect". In the case of deoxyribonucleic acid (DNA), the uptake of the released nucleic acids into the nucleus confers high gene transfer efficiency.

Despite its high gene transfection efficiency, the net positive charge of bPEI-25 has major drawbacks concerning toxicity, aggregation and undesired non-specific interactions of bPEI-25/nucleic acid complexes with cellular and non-cellular components, particular in vivo. Adverse effects include liver necrosis, adhesion of aggregated platelets and shock after systemic injection of higher doses.

In view of the cytotoxic issues faced by bPEI-25, a low molecular weight branched polyethylenimine (Mw about 2.0 kDa, Mn about 1.8 kDa, referred to herein as bPEI-2) has gained interest as well due to its favorable cytotoxicity profile. Low molecular weight enables bPEI-2 to be excreted from the kidneys when used for in vivo therapeutic purposes.

However, the major disadvantage of bPEI-2 is its inefficient transfection ability rendering it inadequate for use as a gene transfection vector.

Thus, an ongoing need exists to develop more efficient and less cytotoxic polyethylenimine derivatives for delivery of biologically active materials.

SUMMARY

Accordingly, a branched polyamine is disclosed, comprising:

about 8 to about 12 backbone tertiary amine groups, about 18 to about 24 backbone secondary amine groups, a positive number n' greater than 0 of backbone terminating primary amine groups, and a positive number q greater than 0 of backbone terminating carbamate groups of formula (2):

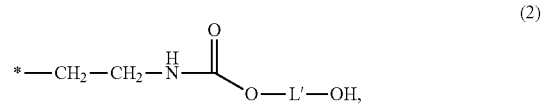

wherein:
(n'+q) is a number equal to about 8 to about 12,
the starred bond of formula (2) is linked to a backbone nitrogen of the branched polyamine,
L' is a divalent linking group comprising 3 to 30 carbons, and
q/(n'+q)×100% equals about 9% to about 40%.

Also disclosed is a branched polyamine, comprising:
about 8 to about 12 backbone tertiary amine groups, about 18 to about 24 backbone secondary amine groups, a positive number n' greater than 0 of backbone terminating primary amine groups, and a positive number q greater than 0 of backbone terminating carbamate groups of formula (4):

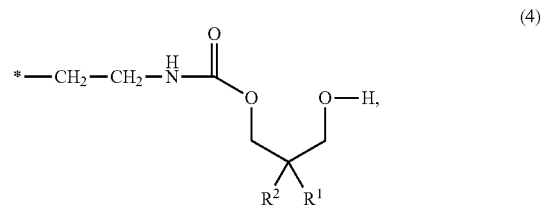

wherein
the starred bond of formula (4) is linked to a backbone nitrogen of the branched polyamine,
$R^1$ is hydrogen, methyl, or ethyl,
$R^2$ is hydrogen or a monovalent radical comprising 1 to 27 carbons,
(n'+q) is a number equal to about 8 to about 12, and
q/(n'+q)×100% equals about 9% to about 40%.

Further disclosed is a method, comprising:
treating a branched first polymer comprising about 8 to about 12 primary amine groups, a plurality of secondary amine groups, and a plurality of tertiary amine groups with a cyclic carbonate monomer without polymerizing the cyclic carbonate monomer, thereby forming a branched polyamine comprising i) about 8 to about 12 backbone tertiary amine groups, ii) about 18 to about 24 backbone secondary amine groups, iii) a positive number n' greater than 0 of backbone terminating primary amine groups, and iv) a positive number q greater than 0 of backbone terminating carbamate groups of formula (2):

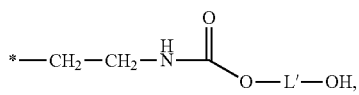

(2)

wherein:

(n'+q) is a number equal to about 8 to about 12, the starred bond of formula (2) is linked to a backbone nitrogen of the branched polyamine, L' is a divalent linking group comprising 3 to 30 carbons, and $q/(n'+q) \times 100\%$ equals about 9% to about 40%.

Also disclosed is a complex, comprising:

a gene; and a branched polyamine comprising about 8 to about 12 backbone tertiary amine groups, about 18 to about 24 backbone secondary amine groups, a positive number n' greater than 0 of backbone terminating primary amine groups, and a positive number q greater than 0 of backbone terminating carbamate groups of formula (2):

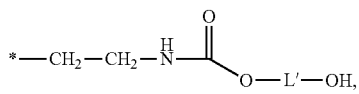

(2)

wherein:

(n'+q) is a number equal to about 8 to about 12, the starred bond of formula (2) is linked to a backbone nitrogen of the branched polyamine, L' is a divalent linking group comprising 3 to 30 carbons, and $q/(n'+q) \times 100\%$ equals about 9% to about 40%.

Also disclosed is a method of treating a cell, comprising contacting the cell with the above-described complex.

Further disclosed is a branched polyamine having a structure according to formula (5):

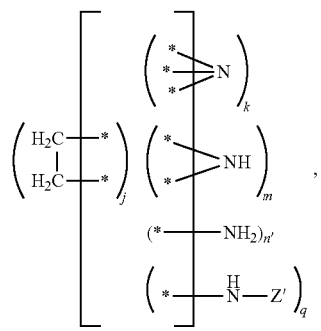

(5)

wherein j, k, m, n' and q represent molar amounts greater than 0, j has a value about 35 to about 47, k has a value of about 8 to about 12, m has a value of about 18 to about 24, (n'+q) has a value of about 8 to about 12, and $q/(n'+q) \times 100\%$ has a value of about 9% to about 40%, and each Z' is an independent moiety selected from the group consisting of

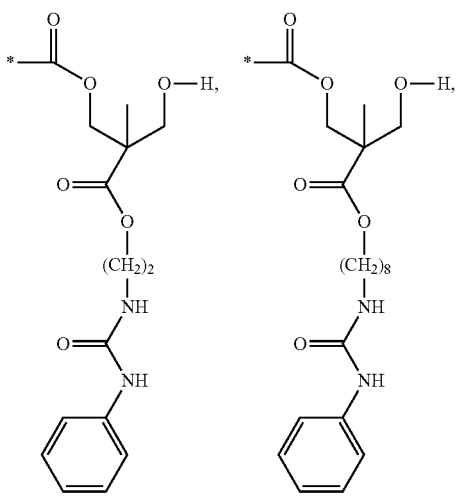

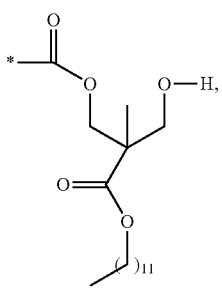

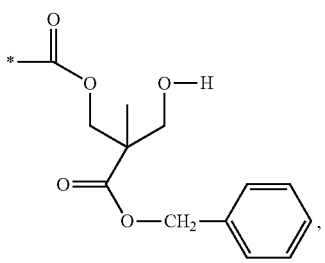

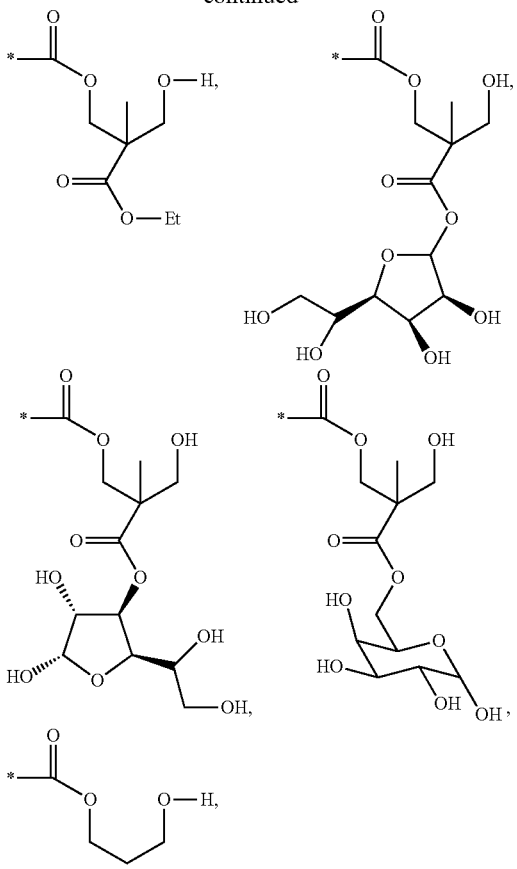

and combinations thereof.

The above-described and other features and advantages of the present invention will be appreciated and understood by those skilled in the art from the following detailed description, drawings, and appended claims.

DETAILED DESCRIPTION

Figure 1:
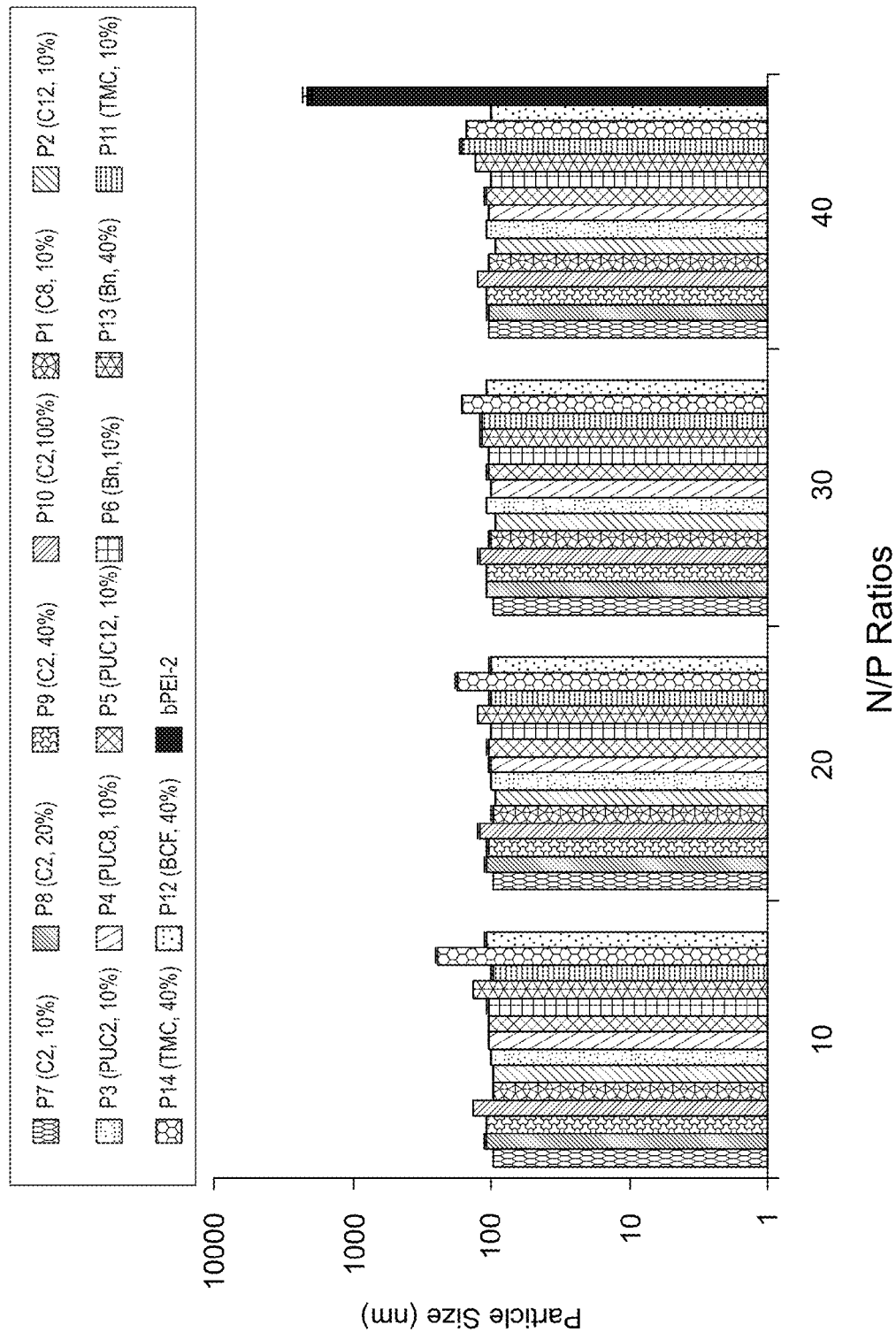
FIG. 1 is a bar graph showing particle sizes of polymer/DNA complexes prepared with luciferase reporter gene and various modified bPEI-2 polymers. Non-modified bPEI-2 is a branched polyethylenimine having a number average molecular weight (Mn)=1.8 kDa, and a weight average molecular weight (Mw)=2000. The cyclic carbonate monomer used to form the modified bPEI-2 polymer is shown in parentheses in the legend. The complexes were prepared at N/P ratios of 10 to 40. A luciferase reporter gene complex of non-modified bPEI-2 was prepared at N/P ratio of 40 as a control.

Disclosed are low molecular weight branched polyamines for delivery of biologically active materials including genes, proteins and/or drugs. The branched polyamines are preferably prepared by reacting one or more hydrophobic cyclic carbonate compounds with a branched polyethylenimine (bPEI) comprising about 8 to about 12 primary amine groups, a plurality of secondary amine groups, and a plurality of tertiary amine groups. For clarity, the branched polyethylenimine starting material for the carbamate forming reaction with the cyclic carbonate monomer is referred to in the following description as a non-modified branched polyethylenimine ("non-modified bPEI"). The product of the reaction is a carbamate functionalized bPEI polymer referred to as a modified branched polyethylenimine ("modified bPEI). The non-modified bPEI can have a number average molecular weight (Mn) of about 1500 to about 2000 and a weight average molecular weight (Mw) of about 1800 to about 4000. More specific branched polyamines are formed by treating bPEI-2 (referred to as "non-modified bPEI-2") with a cyclic carbonate compound. The resulting branched polyamines, which are carbamate functionalized bPEI-2 polymers, are referred to as "modified bPEI-2" polymers. It should be understood that branched amine-containing polymers other than branched polyethylenimines can potentially be used for the carbamate forming reaction (e.g., dendritic amine polymers having about 8 to about 12 primary amine groups, a plurality of secondary amine groups, and a plurality of tertiary amine groups).

The branched polyamines are capable of acting as carriers for genes in a process of gene transfection. The modified bPEIs are attractive for cancer gene therapy applications based on their low cytotoxicity and their efficacy as gene transfection agents in different cancerous cell lines. Exemplary cell lines include cancerous human liver cells (e.g., HepG2) and cancerous human ovarian cells (e.g., SK-OV-3 cells). In some instances, the gene expression levels obtained for the modified bPEI/gene complexes are more than ten-fold higher than the expression level observed for the corresponding non-modified bPEI/gene complex. The modified bPEI/gene complexes also have low cytotoxicity at N/P 10 to N/P 50.

The non-modified bPEI contains a plurality of divalent ethylene groups (*—$CH_2CH_2$—*), a plurality of backbone tertiary amines, a plurality of backbone secondary amines, and a plurality of backbone terminating primary amine groups. More specifically, the non-modified bPEI has about 35 to about 47 ethylene groups, about 8 to about 12 backbone tertiary amine groups, about 18 to about 24 backbone secondary amine groups, and about 8 to about 12 backbone terminating primary amine groups based on the range of Mn and an average ethylenimine subunit having a molecular weight of 43. The backbone end units of the non-modified bPEI contain the primary amine groups.

The non-modified bPEI has a structure consisting essentially of about 8 to about 12 primary ethylenimine repeat units of structure

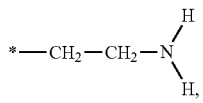

about 18 to about 24 secondary ethylenimine repeat units of structure:

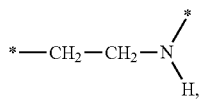

and
about 8 to about 12 tertiary ethylenimine repeat units of structure:

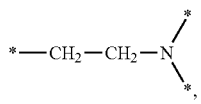

excluding any hydrosalt of the foregoing repeat units that may be present. Each starred bond in the above repeat units represents an attachment point to another repeat unit of the non-modified bPEI.

The non-modified bPEI is also represented herein by formula (1):

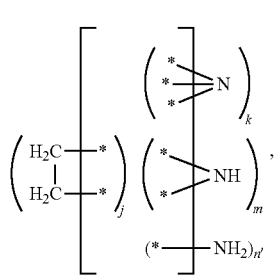

(1)

wherein j, k, m, and n represent moles of the respective independent functional groups of the non-modified bPEI structure, j has a value of about 35 to about 47, k has a value of about 8 to about 12, m has a value of about 18 to about 24, n has a value of about 8 to about 20. It should be understood by the notation of formula (1) that each set of parentheses 0 beginning inside the square brackets [ ] and ending outside the square brackets encloses an independent functional group of the non-modified bPEI, not a polymer chain. The subscripts k, m, n, and j indicate the molar amount of each of the respective independent functional groups of the non-modified bPEI structure. The starred bonds represent attachment points to starred bonds on the opposite side of the brackets. Thus each nitrogen on the right side of the square brackets is bonded to a carbon of an ethylene group on the left side of the square brackets.

As an example, the above-mentioned commercially available branched polyethylenimine bPEI-2 has a weight average molecular weight (Mw) of 2000, a number average molecular weight (Mn) of about 1800, and contains an average of 10 backbone tertiary amine groups, 20 backbone secondary amine groups, 10 backbone terminating primary amine groups, and 35 ethylene groups based on Mn and an average ethylenimine repeat unit molecular weight of 43. In this instance, j=35, k=10, m=20, and n=10. This material is also referred to herein as "non-modified bPEI-2".

As another example, the above-mentioned commercially available branched polyethylenimine bPEI-25 has a weight average molecular weight of 25000, a number average molecular weight of about 10000, and contains an average of 58 backbone tertiary amine groups, 116 backbone secondary amine groups, 58 backbone terminating primary amine groups, and 233 ethylene groups based on Mn and an average ethylenimine repeat unit molecular weight of 43. In this instance, j=233, k=58, m=116, and n=58. This material is also referred to herein as "non-modified bPEI-25".

The backbone terminating primary amine groups of the non-modified bPEI undergo a carbamate forming ring opening reaction with the cyclic carbonate compound, thereby forming a branched polyamine. The ring opening reaction preferably occurs with minimal polymerization or no polymerization of the cyclic carbonate compound.

The branched polyamines contain about 8 to about 12 backbone tertiary amine groups, about 18 to about 24 backbone secondary amine groups, a positive number n' greater than 0 of backbone terminating primary amine groups, and a positive number q greater than 0 of backbone terminating carbamate groups of formula (2):

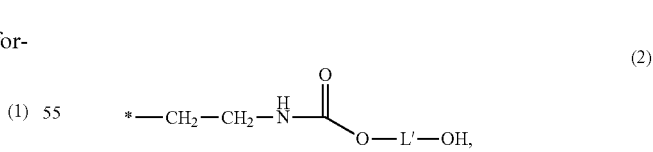

(2)

wherein the starred bond of formula (2) is linked to a backbone nitrogen of the branched polyamine, q/(n'+q)×100% equals about 9% to about 40%, (n'+q) is a number equal to about 8 to about 12, and L' is a divalent linking group comprising 3 to 30 carbons. In an embodiment, L' is a non-charged group. In another embodiment, the modified bPEI comprises no quaternary amine group.

More specific branched polyamines have a structure comprising:

i) a positive number n' greater than 0 of backbone terminating primary ethylenimine repeat units of structure:

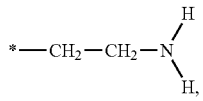

ii) about 18 to about 24 backbone secondary ethylenimine repeat units of structure:

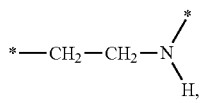

iii) about 8 to about 12 backbone tertiary ethylenimine repeat units of structure:

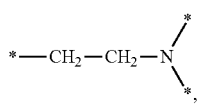

and iv) a positive number q greater than 0 of backbone terminating carbamate end groups of formula (2):

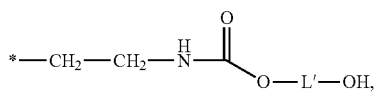

(2)

wherein each of the starred bonds in the above structures represents an attachment point to another repeat unit of the branched polyamine, q/(n'+q)×100% equals about 9% to about 40%, (n'+q) is a number equal to about 8 to about 12, and L' is a divalent linking group comprising 3 to 30 carbons. The starred bond of formula (2) is linked to a backbone nitrogen of the branched polyamine. In an embodiment, the branched polyamine consists essentially of the primary ethylenimine repeat units, secondary ethylenimine repeat units, tertiary ethylenimine repeat units, and carbamate end groups. In another embodiment, the branched polyamine is a carbamate functionalized bPEI-2 (i.e., modified bPEI-2 polymer). In another embodiment, L' is a non-charged group. In another embodiment, the branched polyamine comprises no quaternary amine group.

The branched polyamines can also be represented herein by formula (3):

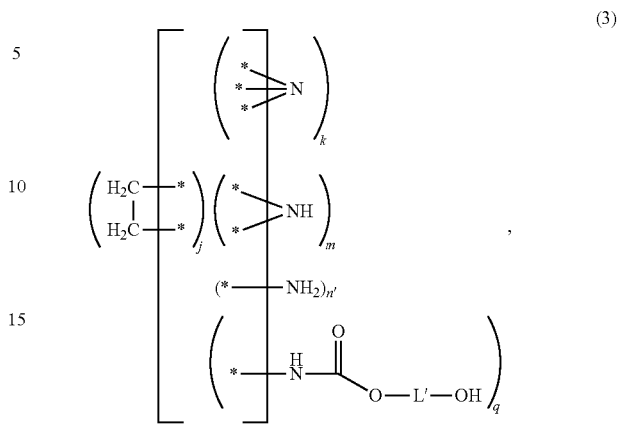

(3)

wherein j, k, m, n' and q represent moles greater than 0 of each of the independent functional groups enclosed in parentheses in formula (3), j has a value of about 35 to about 47, k has a value of about 8 to about 12, m has a value of about 18 to about 24, (n'+q) has a value of about 8 to about 12, and the expression (n'+q)/q×100% has a value of about 9% to about 40%. The notation using the brackets and parentheses has the same meaning as described above for formula (1). L' is a divalent linking group comprising 3 to 30 carbons.

In a method of preparing a branched polyamine, the reaction mixture comprises the cyclic carbonate compound and a non-modified bPEI, and the cyclic carbonate compound is present in an amount less than 50 mol % of the total moles of primary amine groups of the non-modified bPEI. Thus, in this method at least 50% of the primary amine groups of the non-modified bPEI remain non-modified in the branched polyamine. In an embodiment, (n'+q)/q×100% of formula (3) has a value of about 9% to about 25%. In an even more specific embodiment, (n'+q)/q×100% of formula (3) has a value of about 9% to about 12%. In another embodiment q is 1 and n' has a value of about 7 to about 11.

Each backbone tertiary amine group, backbone secondary amine group and/or backbone terminating primary amine group of the branched polyamine can be present as a free base or as a hydrosalt (e.g., a positive charged protonated amine associated with a negative charged counterion such as, for example, hydroxide, chloride, acetate, or sulfonate).

Another more specific branched polyamine comprises about 8 to about 12 backbone tertiary amine groups, about 18 to about 24 backbone secondary amine groups, a positive number n' greater than 0 of backbone terminating primary amine groups, and a positive number q greater than 0 of backbone terminating carbamate groups of formula (4):

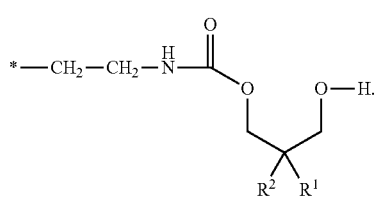

(4)

The starred bond of formula (4) is linked to a backbone nitrogen of the branched polyamine, $R^1$ is hydrogen, methyl, or ethyl, and $R^2$ is hydrogen or a group comprising 1 to 27 carbons, (n'+q) has a value of about 8 to about 12, and q/(n'+q)×100% has a value of about 9% to about 40%. In an embodiment, $R^2$ is an ester *—C(=O)OR$^3$, wherein $R^3$ comprises 1 to 26 carbons.

Another more specific branched polyamine comprises:
i) a positive number n' greater than 0 of backbone terminating primary ethylenimine repeat units of structure:

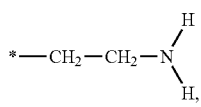

ii) about 18 to about 24 backbone secondary ethylenimine repeat units of structure:

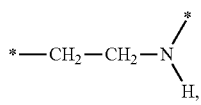

iii) about 8 to about 12 backbone tertiary ethylenimine repeat units of structure:

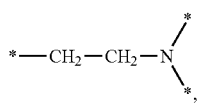

and
iv) a positive number q greater than 0 of backbone terminating carbamate end groups of formula (4):

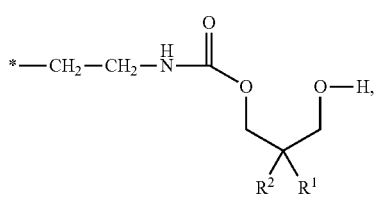

(4)

wherein each of the starred bonds is linked to another repeat unit of the branched polyamine, $R^1$ is hydrogen, methyl, or ethyl, and $R^2$ is hydrogen or a group comprising 1 to 27 carbons, (n'+q) has a value of about 45 to about 70, and q/(n'+q)×100% has a value of about 9% to about 40%. In an embodiment, the branched polyamine consists essentially of the primary ethylenimine repeat units, secondary ethylenimine repeat units, tertiary ethylenimine repeat units, and carbamate end groups. In another embodiment, the branched polyamine is a carbamate functionalized bPEI-2.

In an embodiment, $R^2$ of formula (4) is an ester *—C(=O) OR$^3$, wherein $R^3$ comprises 1 to 26 carbons.

$R^3$ can comprise a sugar moiety. Exemplary $R^3$ groups comprising sugar moieties include esters of mannose, galactose, or glucose.

$R^3$ can comprise a monovalent hydrocarbon radical comprising 1 to 26 carbons. Exemplary monovalent hydrocarbon radicals include methyl, ethyl, propyl, butyl, pentyl, hexyl, septyl, octyl, nonyl, decyl, undecyl and dodecyl groups. The monovalent hydrocarbon radical can be branched or straight chain.

Other $R^3$ groups include benzyl esters and esters bearing a urea group.

The branched polyamine can have a number average molecular weight (Mn) of about 1600 to about 5000. The modified bPEI can have a weight average molecular weight (Mw) of about 2100 to about 6000.

The carbamate group can optionally comprise one or more protecting groups. In these instances, the method of forming a branched polyamine can further comprise selectively removing the one or more protecting groups.

Exemplary cyclic carbonate monomers include the compounds of Table 1:

TABLE 1

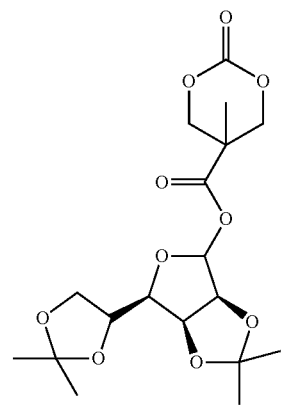

MTC-IPMAN

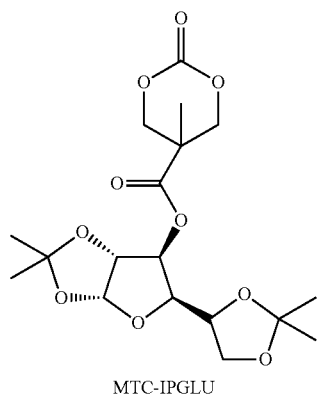

MTC-IPGLU

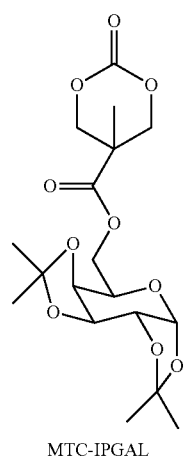

MTC-IPGAL

TABLE 1-continued
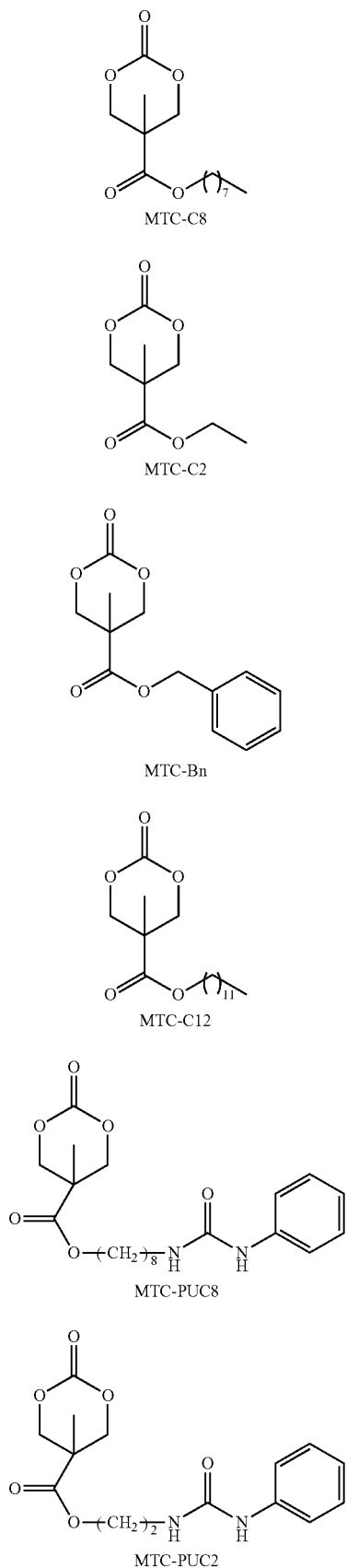
TABLE 1-continued
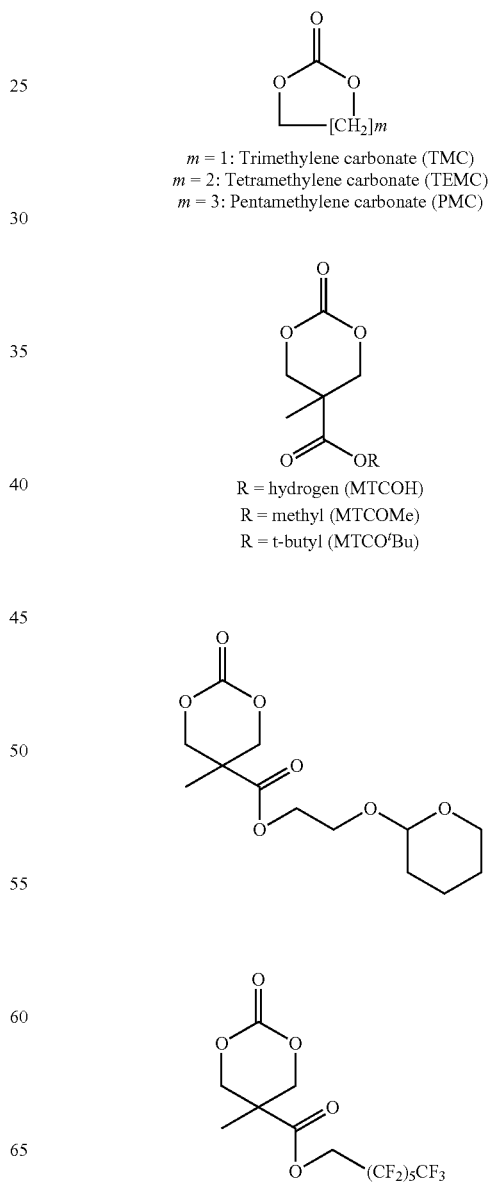
Additional examples of cyclic carbonate monomers include the compounds of Table 2.
TABLE 2

TABLE 2-continued
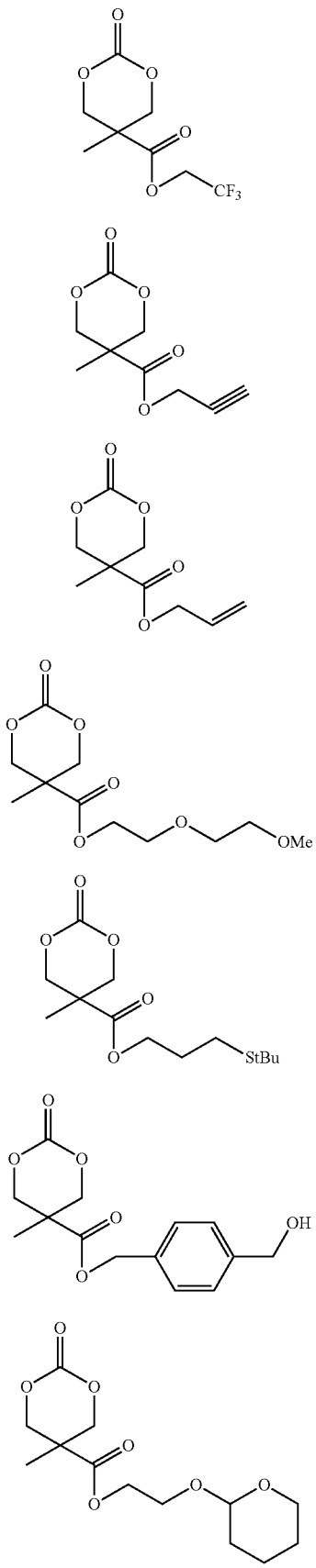
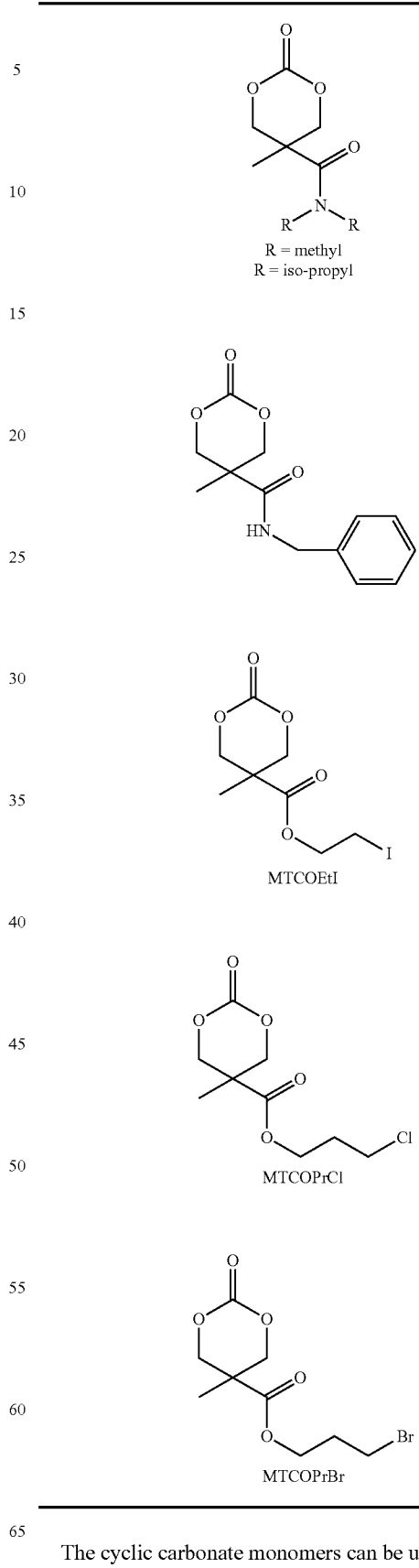
The cyclic carbonate monomers can be used singularly or in combination.

More specific branched polyamines have a structure according to formula (5):

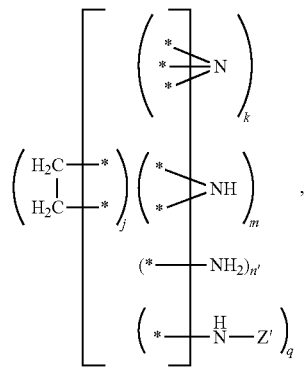

wherein j, k, m, n' and q represent molar amounts greater than 0, j is a number having a value of about 35 to about 47, k is a number having a value of about 8 to about 12, m is a number having a value of about 18 to about 24, (n'+q) has a value of about 8 to about 12, the expression (n'+q)/q×100% has a value of about 9% to about 40%, and each Z' is a moiety independently selected from the group consisting of

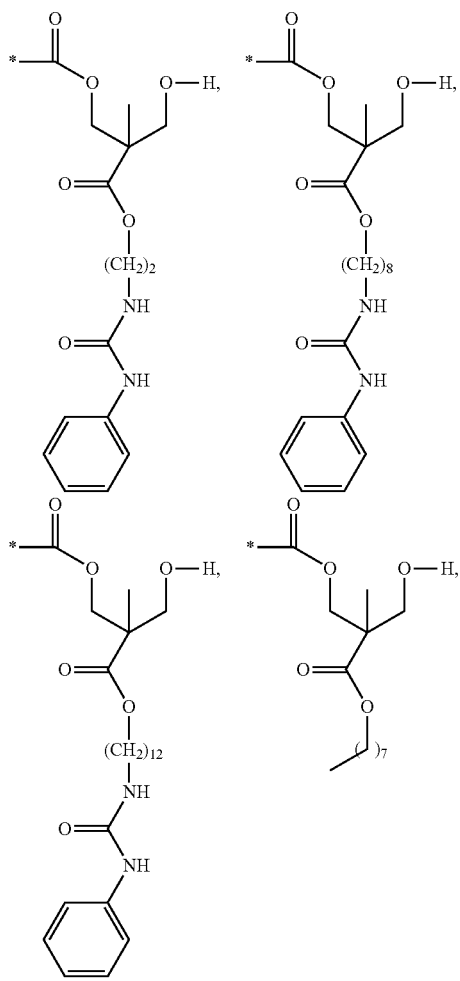

and combinations thereof.

Also disclosed is a complex comprising a gene and the above-described branched polyamine. Further disclosed is a method of treating a cell, comprising contacting the cell with the complex.

The following examples demonstrate a facile method of introducing hydrophobic carbamate groups into non-modified bPEI-2 using cyclic carbonates. The cyclic carbonates can be ring opened with or without organic catalyst (1,8-diazabicycloundec-7-ene, DBU). Without DBU, a carbamate with a primary alcohol can form. With DBU, a carbamate with a primary alcohol can also form when the primary amine groups are present in excess of the cyclic carbonate. However, if the cyclic carbonate is present in excess of the primary amine groups, the resulting branched polyamine is likely to contain poly(carbonate) chains linked to the primary amine sites.

DNA binding, particle size, zeta potential, and gene expression properties of various modified bPEI-2/gene complexes are described. The gene transfection efficiency and cytotoxicity of the modified bPEI-2 complexes in HepG2 (human liver carcinoma cell line) and SK-OV-3 (human ovarian carcinoma cell line) were investigated and compared with the non-modified bPEI-2 by using luciferase reporter gene and green fluorescent protein (GFP) reporter gene.

EXAMPLES

Materials used in the following examples are listed in Table 3.

TABLE 3

| ABBREVIATION | DESCRIPTION | SUPPLIER |
|---|---|---|
| DBU | 1,8-Diazabicyclo[5,4,0]undec-7-ene | Aldrich |
| bPEI-25 | Branched Polyethylenimine, Mw = 25 kDa, Mn = 10 kDa, 58 primary amine groups, 116 secondary amine groups and 58 tertiary amine groups; also referred to as non-modified bPEI-25. | Aldrich |
| bPEI-2 | Branched Polyethylenimine, Mw = 2 kDa, Mn = 1.8 kDa, 10 primary amine groups, 20 secondary amine groups, and 10 tertiary amine groups; also referred to as non-modified bPEI-2. | Aldrich |
| MTT | 1-(4,5-Dimethylthiazol-2-yl)-3,5-Diphenylformazan | Aldrich |
| MTC-OH | 5-Methyl-5-Carboxyl-1,3-Dioxan-2-One | |
| | 2-Amino-1-Ethanol | Aldrich |
| | 8-Amino-1-Octanol | Aldrich |
| | 12-Amino-1-Dodecanol | Aldrich |
| TMC | Trimethylene Carbonate | Aldrich |
| Bis-MPA | 2,2-Dimethylol-Propionic Acid | Aldrich |
| DBU | 1,8-Diazabicyclo[5,4,0]Undec-7-Ene | Aldrich |
| PFC | Bis-(Pentafluorophenyl) Carbonate | Aldrich |

Herein, Mn is the number average molecular weight, Mw is the weight average molecular weight, and MW is the molecular weight of one molecule.

1,8-Diazabicyclo[5,4,0]undec-7-ene (DBU) was stirred over $CaH_2$ and vacuum distilled before being transferred to a glove box. Branched polyethylenimines having a weight average molecular weight of 25 kDa (bPEI-25) and 1.8 kDa (bPEI-2), 1-(4,5-dimethylthiazol-2-yl)-3,5-diphenylformazan (MTT) for cytotoxicity assay, and other reagents for polymer synthesis were commercially available from Aldrich and used without any other purification unless otherwise noted. Luciferase substrate and 5× lysis buffer was purchased from Promega (Singapore). GFP-reporter gene (encoding a red-shifted variant of wild-type GFP driven by the cytomegalovirus promoter) and luciferase-reporter gene (encoding the 6.4 kb firefly luciferase gene driven by the cytomegalovirus promoter) were obtained from Clontech (U.S.A.) and Carl Wheeler, Vical (U.S.A.) respectively. The BCA protein assay kit was from Pierce. HepG2 and SK-OV-3 human cancer cell lines were purchased from ATCC (U.S.A.).

MTC-OH can be prepared by the method of R. C. Pratt, et al., Chemical Communications, 2008, 114-116.

Preparation of MTC-$C_6H_5$ (MW 326.2)

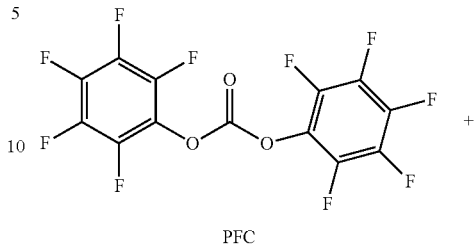

A 100 mL round bottom flask was charged with bis-MPA, (7), (5.00 g, 37 mmol, MW 134.1), bis-(pentafluorophenol) carbonate (PFC, 31.00 g, 78 mmol, MW 394.1), and CsF (2.5 g, 16.4 mmol) rinsed in with 70 mls of tetrahydrofuran (THF). Initially the reaction was heterogeneous, but after one hour a clear homogeneous solution was formed that was allowed to stir for 20 hours. The solvent was removed in vacuo and the residue was re-dissolved in methylene chloride. The solution was allowed to stand for approximately 10 minutes, at which time the pentafluorophenol byproduct precipitated and could be quantitatively recovered. This pentafluorophenol byproduct showed the characteristic 3 peaks in the $^{19}F$ NMR of pentafluorophenol and a single peak in the GCMS with a mass of 184. The filtrate was extracted with sodium bicarbonate, water and was dried with $MgSO_4$. The solvent was evaporated in vacuo and the product was recrystallized (ethyl acetate/hexane mixture) to give MTC-C6F5 as a white crystalline powder. The GCMS had a single peak with mass of 326 g/mol. The calculated molecular weight for $C_{12}H_7F_5O_5$ was consistent with the assigned structure. $^1$H-NMR (400 MHz in $CDCl_3$): delta 4.85 (d, J=10.8 Hz, 2H, $CH_aH_b$), 4.85 (d, J=10.8 Hz, 2H, $CH_aH_b$), 1.55 (s, 3H, $CCH_3$).

I. Synthesis of Monomers

Example 1

Preparation of MTC-Cl (MW 178.6)

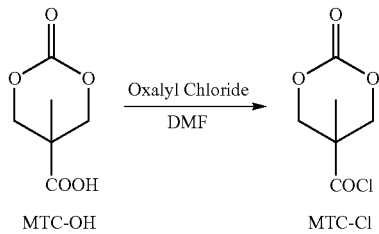

A solution of oxalyl chloride (2.48 mL, 19.0 mmol) in 50 mL of dry tetrahydrofuran (THF) was added dropwise into a solution of 5-methyl-5-carboxyl-1,3-dioxan-2-one, (MTC-OH) (2.75 g, 17.2 mmol, MW 160.1) in 50 mL of dry THF, followed by adding a catalytic amount (3 drops) of anhydrous dimethylformamide (DMF) over 30 min under nitrogen atmosphere. The reaction solution was stirred for 1 hour with $N_2$ bubbled through to remove volatiles. After the reaction, the solvent was evaporated under vacuum yielding MTC-C1, which was not further purified.

Example 2

Preparation of MTC-C2 (MW 188.2)

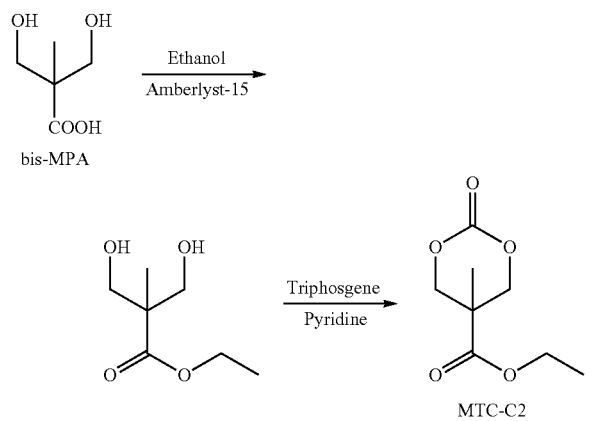

I) bis-MPA (22.1 g, 0.165 mol, MW 134.1) was added to ethanol (150 mL) with Amberlyst-15 (6.8 g), and refluxed overnight. The resins were then filtered out and the filtrate was evaporated. Dichloromethane (200 mL) was added to the resulting viscous liquid to filter the unreacted reagent and byproduct. After the solution was dried over MgSO4 and evaporated, ethyl 2,2-bis(methylol)propionate (MW 162.2) was obtained as a clear and colorless liquid (24.3 g, 91%). $^1$H NMR (400 MHz, CDCl3, 22° C.): delta 4.09 (q, 2H, —OCH2CH3), 3.74 (d, 2H, —CH2OH), 3.57 (d, 2H, —CH2OH), 1.18 (t, 3H, —OCH2CH3), 0.98 (s, 3H, —CH3).

II) A solution of triphosgene (11.7 g, 0.039 mol) in dichloromethane (150 mL) was added dropwise to a dichloromethane solution (150 mL) of ethyl 2,2-bis(methylol)propionate (12.6 g, 0.078 mol, MW 162.2) and pyridine (39 mL, 0.47 mol) over 30 min at −75° C. with dry ice/acetone under nitrogen atmosphere. The reaction mixture was kept stirring for another 2 hours under chilled conditions and then allowed to warm up to room temperature. The reaction was quenched by addition of saturated aqueous NH4Cl (75 mL), after which the organic layer was washed with 1 M aqueous HCl (3×100 mL), saturated aqueous NaHCO3 (1×100 mL), dried over MgSO4, filtered and evaporated. The residue was recrystallized from ethyl acetate to give MTC-C2 (MW 188) as white crystals (8.0 g, 55%). $^1$H NMR (400 MHz, CDCl3, 22° C.): delta 4.67 (d, 2H, —CH2OCOO), 4.25 (q, 2H, —OCH2CH3), 4.19 (d, 2H, —CH2OCOO), 1.30 (s, 3H, —CH3), 1.27 (t, 3H, —OCH2CH3).

Example 3

Preparation of MTC-C8 (MW 272.3)

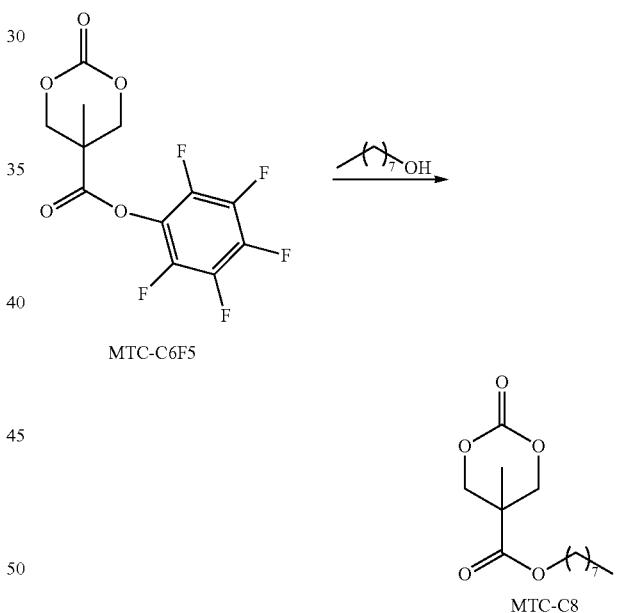

A flask was charged with MTC-C6F5 (5.5 g, 16.9 mmol, MW 326.2), octanol (2.0 g, 15.4 mmol), PROTON SPONGE (3.29 g, 15.4 mmol) and THF (8 mL). The reaction mixture was stirred for 12 hours and excess ammonium acetate was added. The reaction mixture was stirred for 3 additional hours and then added directly to a silica gel column. The product was isolated by column chromatography using hexane/ethyl acetate as the eluent to yield an oil. MTC-C8 $^1$H NMR (400 MHz, CDCl3, 22° C.): delta 4.71 (d, 2H, —CH2OCOO), 4.23 (d, 2H, —CH2OCOO), 4.22 (t, 2H, —OCH2CH2), 1.68 (t, 2H, —OCH2CH2(CH2)5), 1.36 (s, 3H, —CH3), 1.31 (t, 10H, —CH2(CH2)5 CH3), 0.90 (t, 3H, —(CH2)5CH3).

Example 4

MTC-C12 (MW 328.4) was Synthesized Using the General Procedure of Example 3, Replacing Ethanol with Dodecanol

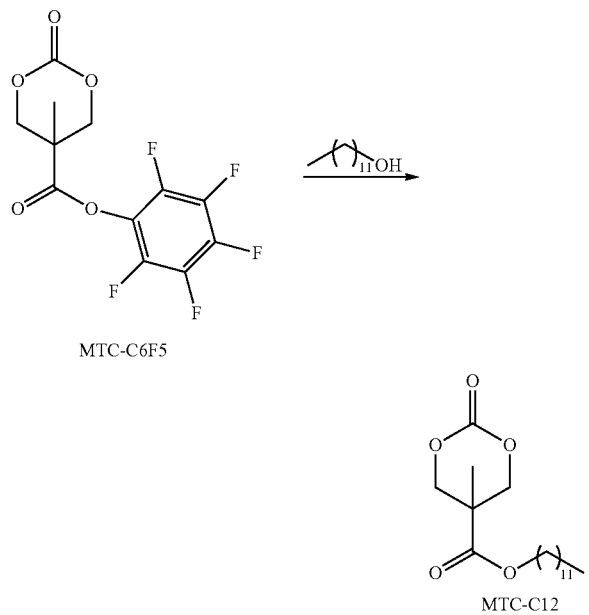

MTC-C12 $^1$H NMR (400 MHz, CDCl3, 22° C.): delta 4.69 (d, 2H, —CH2OCOO), 4.23 (d, 2H, —CH2OCOO), 4.21 (t, 2H, —OCH2CH2), 1.68 (t, 2H, —OCH2CH2(CH2)5), 1.35 (s, 3H, —CH3), 1.28 (t, 10H, —CH2(CH2)5 CH3), 0.90 (t, 3H, —(CH2)5CH3).

Example 5

Synthesis MTC-Bn (MW 250.3)

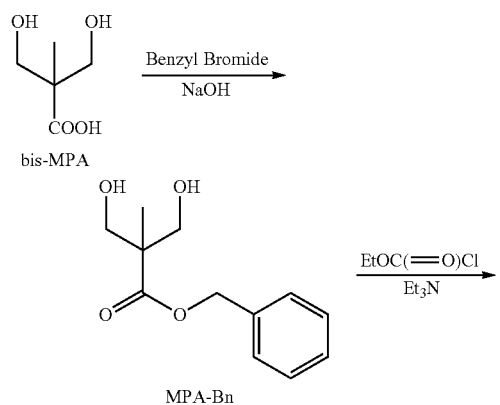

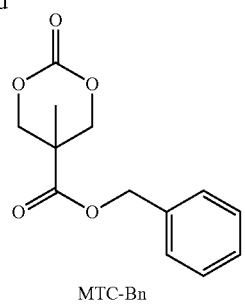

2,2-Bis(methylol)propanoic acid (bis-MPA) (20 g, 149.1 mmol, MW 134.1) and sodium hydroxide (5.96 g, 149.1 mmol) were combined in 100 mL DMSO and let stir overnight at 80° C. Benzyl Bromide (30.6 g, 178.9 mmol) was added dropwise. The solution cleared and the reaction was monitored by NMR. Once the reaction was complete, the solution was cooled to room temperature and 500 mL of water was added. The solution was extracted with diethyl ether several times and the diethyl ether solution was concentrated down to 250 mL. This solution was washed with water, sodium bicarbonate, and brine solutions, dried, and concentrated down to a solid. The solid was recrystallized out of THF/Hexanes to obtain white crystals of MPA-Bn (10.0 g, 30%). MPA-Bn (4.76 g, 21.2 mmol, MW 224.3) and triethylamine (5.4 g, 53.1) were then dissolved in dry THF (210 mL) and cooled to 0° C. Under nitrogen, ethyl chloroformate (5.1 g, 46.7 mmol) was added dropwise to the stirring solution. The solution was warmed to room temperature and reacted for 18 hours. The reaction solution was then concentrated down to a solid, and the solid was recrystallized twice out of diethyl ether to yield MTC-Bn as white crystals (3.86 g, 72.6%). $^1$H NMR (400 MHz, CDCl$_3$, 22° C.): delta 7.38 (m, 2H, C5H6), 5.24 (s, 2H, —OCH2C5H6) 4.72 (d, 2H, —CH2OCOO), 4.21 (d, 2H, —CH2OCOO), 4.21 (t, 2H, —OCH2C5H6), 1.36 (s, 3H, —CH3).

Cyclic carbonate monomers having protected sugar pendant groups include MTC-IPMAN, MTC-IPGAL and MTC-IPGLU.

Example 6

The Preparation of MTC-IPMAN (MW 402.3)

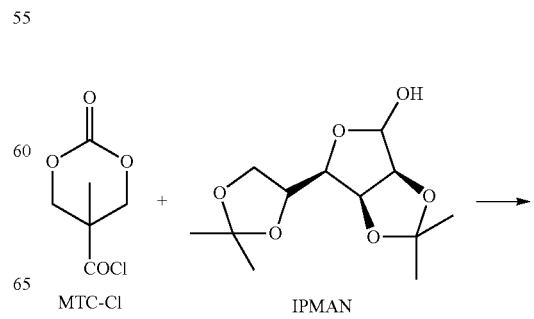

-continued

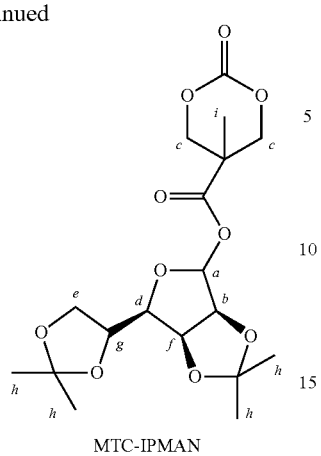

MTC-IPMAN

The preparation of MTC-IPMAN is representative. MTC-Cl was formed as described above and dissolved in 50 mL of dry dichloromethane (DCM). A mixture of 2,3;5,6-di-O-isopropylidene-D-mannofuranose (IPMAN) (4.13 g, 15.8 mmol, MW 260.3) and triethylamine (2.8 mL, 20.6 mmol) in 50 mL of dry dichloromethane (DCM) was added dropwise into the solution over 30 minutes at room temperature. Then, the reaction mixture was heated to 40° C. for 48 hours. After cooling the mixture to room temperature, the solution was concentrated and 100 mL THF was added to precipitate the triethylamine salt. After filtration of the salt and removal of the solvent, the resulting crude product was passed through a silica gel column by gradient eluting using ethyl acetate and hexane (20/80 to 50/50) to provide the product as sticky colorless oil that slowly solidified to a white solid (5.85 g, 85%). $^1$H-NMR (400 MHz, CDCl$_3$, 22° C.): delta 6.17 (s, 1H, H-a), 5.79 (dd, 1H, H-b), 4.83 (m, 1H, H-d), 4.66 (d, 2H, H-c), 4.41 (m, 1H, H-g), 4.22 (m, 2H, H-c), 4.03 (m, 2H, H-e+H-f), 3.73 (m, 1H, H-e), 1.33-1.50 (m, 15H, H-h+H-i).

Example 7

Preparation of MTC-IPGAL (MW 402.2)

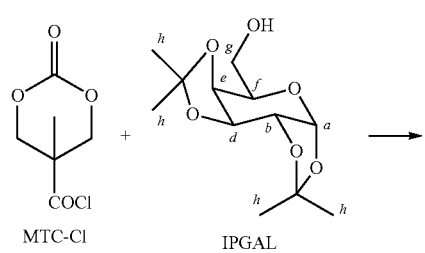

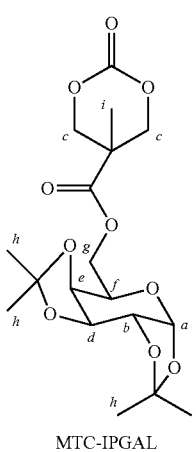

MTC-IPGAL

MTC-IPGAL was prepared using the procedure of Example 6 and 1,2;3,4-Di-O-isopropylidene-D-galactopyranose (IPGAL, MW 260.3). Yield 81%. $^1$H-NMR (400 MHz, CDCl$_3$, 22° C.): delta 5.54 (d, 1H, H-a), 4.70 (m, 2H, H-c), 4.62 (m, 1H, H-b), 4.41 (m, 1H, H-f), 4.33 (m, 2H, H-d and H-e), 4.26 (m, 3H, H-c and H-g), 4.03 (m, 1H, H-g), 1.32-1.49 (5 s, 15H, H-h+H-i).

Example 8

Preparation of MTC-IPGLU (MW 402.2)

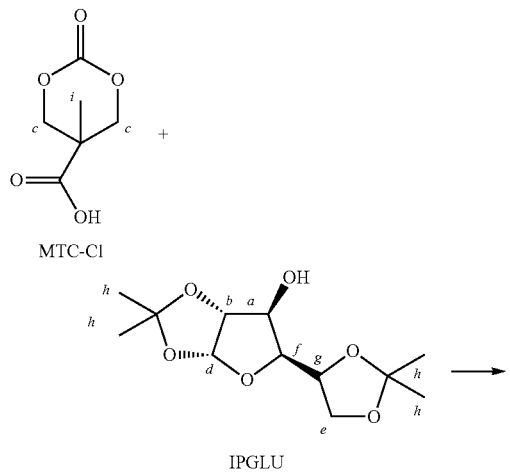

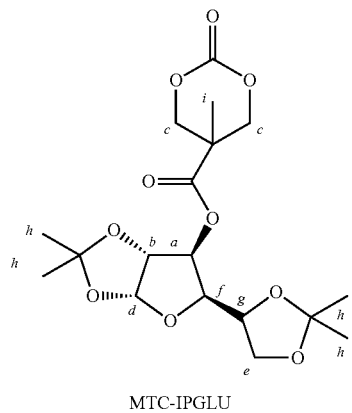

MTC-IPGLU

MTC-IPGLU was prepared using the procedure of Example 6 and 1,2;5,6-Di-O-isopropylidene-D-glucofuranose (IPGLU, MW 260.3). Yield 75%. $^1$H-NMR (400 MHz, CDCl$_3$, 22° C.): delta 5.90 (d, 1H, H-a), 5.39 (d, 1H, H-b), 4.69 (d, 2H, H-c), 4.46 (d, 1H, H-g), 4.18 (m, 2H, H-c), 4.06 (m, 2H, H-e and H-f), 4.00 (m, 1H, H-e), 1.30-1.52 (5s, 15H, H-h+H-i).

Cyclic carbonates having a pendant phenylurea group were prepared according to Scheme 1.

Scheme 1.

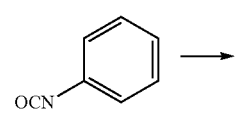

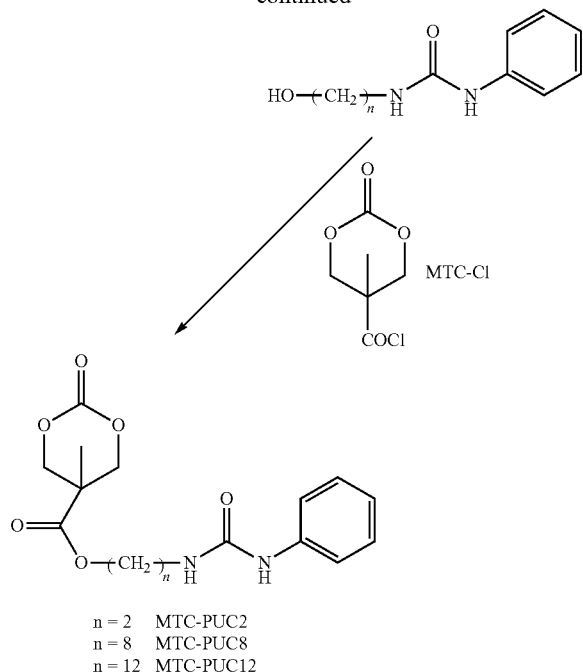

n = 2 MTC-PUC2
n = 8 MTC-PUC8
n = 12 MTC-PUC12

Example 9

Synthesis of MTC-PUC2 (MW 322.3)

1) Ethanolamine (5.0 g, 48.5 mmol, 1 eq) was placed in a dry 100 mL round bottom flask equipped with a stir bar, and dry THF (30 mL) was added. The resulting solution was chilled to 0° C. via an ice bath. Phenylisocyanate (5.19 g, 4.74 mL, 43.6 mmol, 0.9 equivalents) and 30 mL of dry THF was added dropwise to the ethanolamine/THF mixture through a dropping funnel over 30 min. The resulting mixture was left to warm to ambient temperature and allowed to stand under stirring for an additional 16 hours. Rotational evaporation was used to remove THF. The resulting crude product was recrystallized from ethyl acetate before being stirred vigorously for an additional 4 hours. The recrystallized solids were isolated by filtration and further washed with ethyl acetate and dried until a constant weight was reached, giving a yield of 7.0 g (~80%) intermediate phenylureaethanol (n=2 in Scheme 1). $^1$H-NMR (400 MHz, DMSO-$d_6$, 22° C.): delta 8.55 (s, 1H, —NHPh), 7.36 (d, 2H, PhH), 7.20 (t, 2H, PhH), 6.88 (t, 1H, PhH), 6.18 (t, 1H, —CH$_2$NHCO—), 4.76 (t, 1H, —OH), 3.43 (q, 2H, —CH$_2$OH), 3.15 (q, 2H, —CH$_2$NHCO—).

2) MTC-OH (4.3 g, 26.8 mmol) was converted to MTC-Cl by using oxalyl chloride as described above. The MTC-Cl was dissolved in 50 mL of dry methylene chloride and charged in an additional funnel. In a dry 500 mL round bottom flask equipped with a stir bar was charged phenylureaethanol (5.55 g, 25 mmol), pyridine (1.97 g, 2.02 mL, 25 mmol) and dry methylene chloride (150 mL). The additional funnel was attached under nitrogen and the flask cooled to 0° C. using an ice bath. The MTC-Cl solution was added dropwise during a period of 30 minutes and the resulting solution was stirred an additional 30 minutes. The ice bath was removed and the solution was allowed to warm up to ambient temperature and left under stirring for an additional 16 hours. The crude product was purified by column chromatography using silica gel. Methylene chloride was initially used as eluent before gradually increasing the polarity finishing with a final concentration of 5 vol % methanol. The product fractions were collected and the solvent was removed through rotational evaporation. The isolated product was dried under vacuum until a constant weight was reached yielding 8.0 g (about 80%) of an off-white/yellowish oil which crystallized upon standing. $^1$H-NMR (400 MHz, DMSO-$d_6$, 22° C.): delta 8.59 (s, 1H, —NHPh), 7.38 (d, 2H, PhH), 7.21 (t, 2H, PhH), 6.89 (t, 1H, PhH), 6.26 (t, 1H, —CH$_2$NHCO—), 4.57 (d, 2H, —COOCH$_2$CH$_2$—), 4.35 (d, 2H, —CH$_2$OCOO—), 4.16, (t, 2H, —CH$_2$OCOO—), 3.35 (q, 2H, —CH$_2$NHCO—), 1.20 (s, 3H, —CH$_3$).

Example 10

MTC-PUC8 (MW 406.5) was prepared using the procedure of Example 9 and 8-amino-1-octanol. Yield, 86%, $^1$H-NMR (400 MHz, DMSO-$d_6$, 22° C.): delta 8.37 (s, 1H, —NHPh), 7.38 (d, 2H, PhH), 7.21 (t, 2H, PhH), 6.86 (t, 1H, PhH), 6.10 (t, 1H, —CH$_2$NHCO—), 4.57 (d, 2H, —COOCH$_2$CH$_2$—), 4.39 (d, 2H, —CH$_2$OCOO—), 4.17, (t, 2H, —CH$_2$OCOO—), 3.06 (q, 2H, —CH$_2$NHCO—), 1.26-1.40 (2s, 15H, —(CH$_2$)$_6$— and —CH$_3$).

Example 11

MTC-PUC12 (MW 462.6) was prepared using the procedure of Example 9 and 12-amino-1-dodecanol. Yield, 65%, $^1$H-NMR (400 MHz, DMSO-$d_6$, 22° C.): delta 8.37 (s, 1H, —NHPh), 7.34 (d, 2H, PhH), 7.17 (t, 2H, PhH), 6.83 (t, 1H, PhH), 6.09 (t, 1H, —CH$_2$NHCO—), 4.51 (d, 2H, —COOCH$_2$CH$_2$—), 4.33 (d, 2H, —CH$_2$OCOO—), 4.09, (t, 2H, —CH$_2$OCOO—), 3.02 (q, 2H, —CH$_2$NHCO—), 1.28-1.56 (m, 23H, —(CH$_2$)$_{10}$— and —CH$_3$).

Modification with MTC-C8 and MTC-C12 bPEI-2 has 10 primary amine groups, 20 secondary amine groups and 10 tertiary amine groups per mole based on 1 mole=1800 (Mn). bPEI-2 was modified with cyclic carbonate monomers bearing hydrophobic ester groups of different chain lengths according to Scheme 2.

Scheme 2.

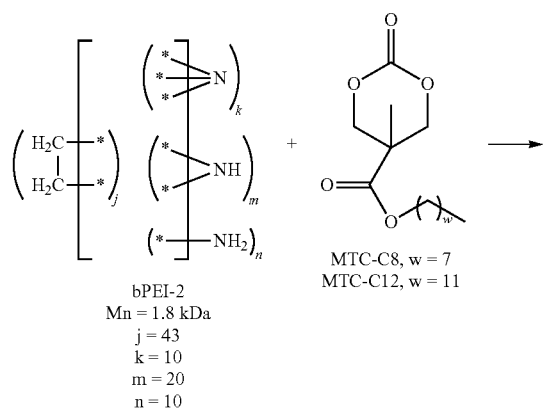

bPEI-2
Mn = 1.8 kDa
j = 43
k = 10
m = 20
n = 10

MTC-C8, w = 7
MTC-C12, w = 11

Scheme 3.

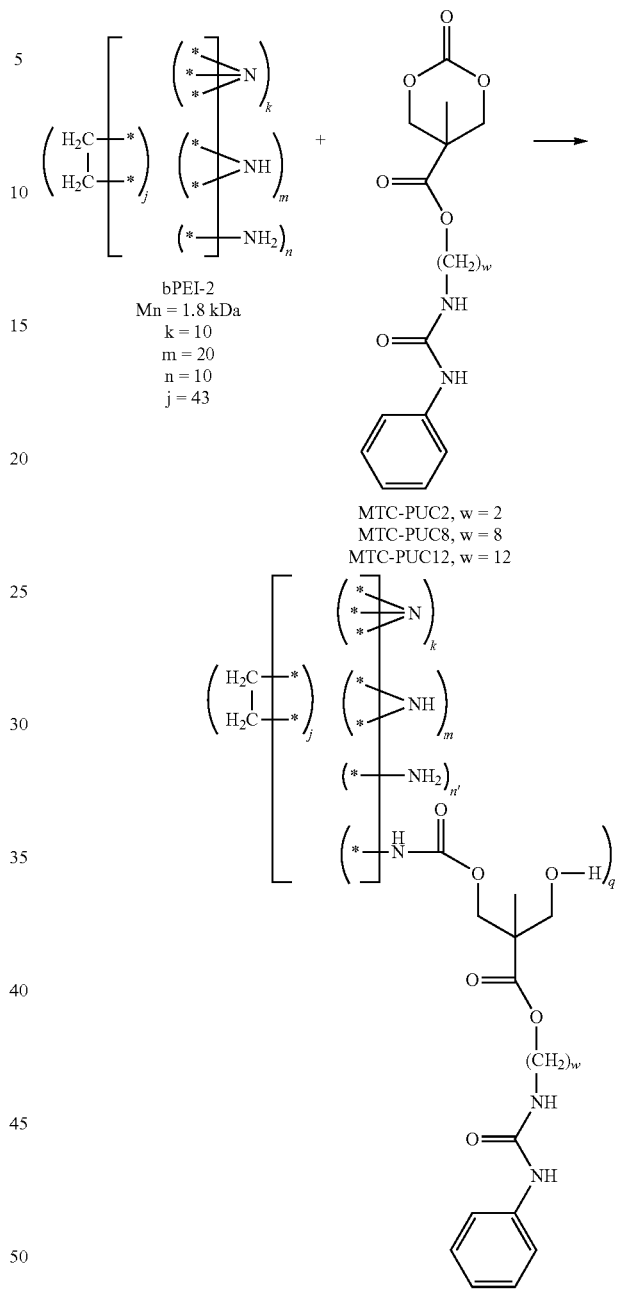

MTC-PUC2, w = 2
MTC-PUC8, w = 8
MTC-PUC12, w = 12

P3, w = 2
P4, w = 8
P5, w = 12

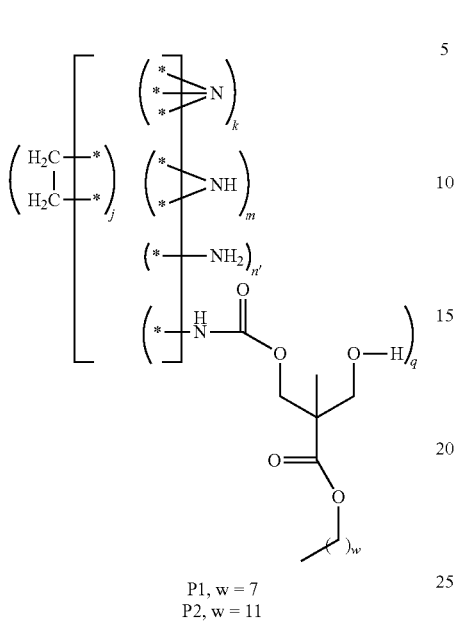

P1, w = 7
P2, w = 11

Example 12

The procedure to form P1 using MTC-C8 is representative. In a glove box, MTC-C8 (0.0408 g, 0.15 mmol, MW=272 g) was added to the solution of bPEI-2 (0.270 g, 0.15 mmol based on 1 mole=1800 g=Mn) in 2 mL of DCM. The bPEI-2:MTC-C8 molar feed ratio was 1:1 and the mass feed ratio was 6.6:1. The reaction solution was stirred for 1 hour. The polymers were precipitated in anhydrous ether and dried by rotary evaporation. The molar ratio found by NMR for polymer P1 was 1:1. Therefore, m=20, q=1, n'=9, k=10, and j=43 for polymer P1 of Scheme 2.

Example 13

Polymer P2 prepared with MTC-C12 following the general procedure of Example 12. The bPEI-2:MTC-C12 molar feed ratio was 1:1 and the mass feed ratio was 5.5:1. The molar ratio found by NMR for polymer P2 was 1:0.86. Therefore, m=20, q=0.86, n'=9.14, k=10, and j=43 for polymer P2 of Scheme 2.

Modification with MTC-PUC2, MTC-PUC8 and MTC-PUC12.

bPEI-2 was modified with cyclic carbonate monomers bearing hydrophobic urea-containing ester groups of different chain lengths according to Scheme 3 to produce branched polyamines P3 to P5 using the general procedure of Example 12. The reaction time was 1 hour. The polymers were precipitated in anhydrous ether and dried by rotary evaporation.

Example 14

For polymer P3, the bPEI-2:MTC-PUC2 molar feed ratio was 1:1 and the mass feed ratio was 5.6:1. The molar ratio found by NMR for polymer P3 was 1:0.9. Therefore, m=20, q=0.9, n'=9.1, k=10, and j=43 for polymer P3 of Scheme 3.

Example 15

For polymer P4, the bPEI-2:MTC-PUC8 molar feed ratio was 1:1 and the mass feed ratio was 4.4:1. The molar ratio found by NMR for polymer P4 was 1:0.9. Therefore, m=20, q=0.9, n'=9.1, k=10, and j=43 for polymer P4 of Scheme 3.

Examples 16

For polymer P5, the bPEI-2:MTC-PUC12 molar feed ratio was 1:1 and the mass feed ratio was 3.9:1. The molar ratio found by NMR for polymer P5 was 1:1.1. Therefore, m=20, q=1.1, n'=8.9, k=10, and j=43 for polymer P5 of Scheme 3.
Modification with MTC-Bn bPEI-2 was modified with MTC-Bn (MW 250) according to Scheme 4 using the general procedure of Example 12 to produce branched polyamines P6 and P13. The reaction time was 1 hour. The polymers were precipitated in anhydrous ether and dried by rotary evaporation.

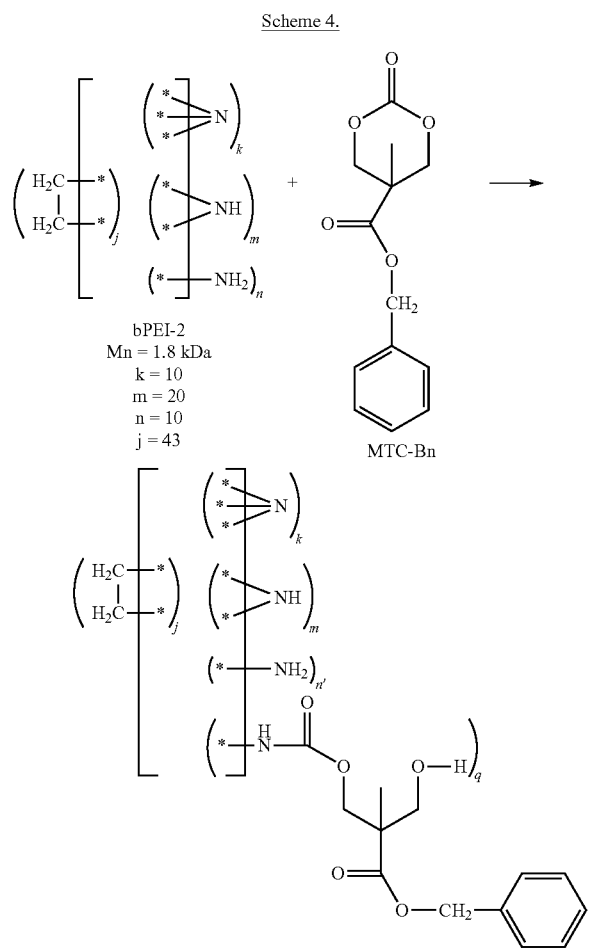

Scheme 4.

Examples 17

For the preparation of P6, the bPEI-2:MTC-Bn molar feed ratio was 1:1 and the mass feed ratio was 7.2:1. The bPEI-2:MTC-Bn molar ratio found by NMR for P6 was 1:1.1. Therefore, m=20, q=1.1, n'=8.9, k=10, and j=43 in Scheme 4 for P6.

Example 18

For the preparation of P13, the bPEI-2:MTC-Bn molar feed ratio was 1:4 and the mass feed ratio of 1.8:1. The bPEI-2:MTC-Bn molar ratio found by NMR was 1:4.7 for P13. Therefore, m=20, q=4.7, n'=5.3, k=10, and j=43 in Scheme 4 for P13.
Modification with MTC-C2 bPEI-2 was modified with MTC-C2 according to Scheme 5 using the general procedure of Example 12 to produce branched polyamines P7 to P10. The reaction time was 1 hour. The polymers were precipitated in anhydrous ether and dried by rotary evaporation.

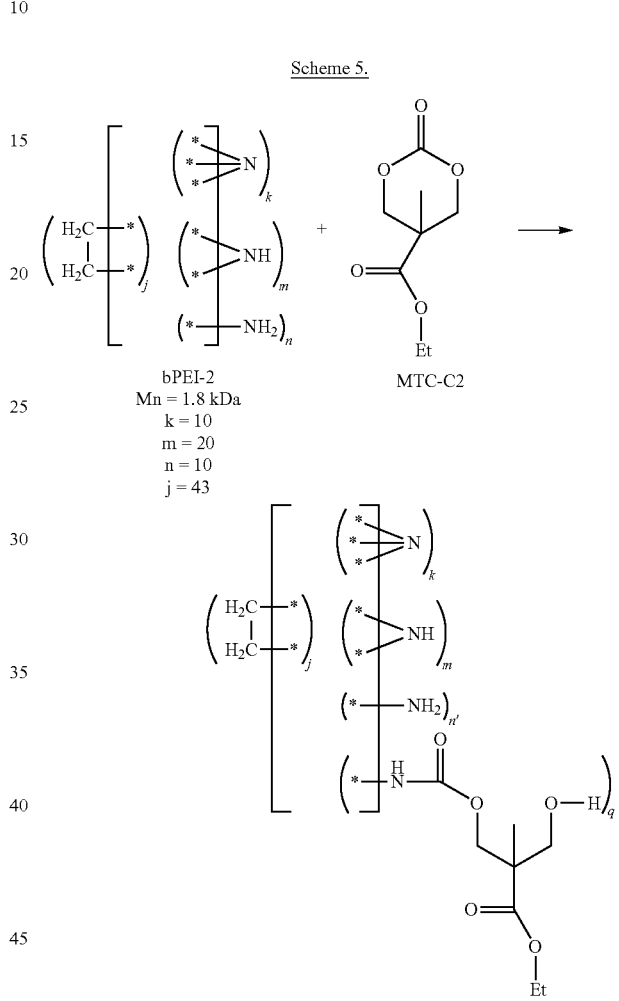

Scheme 5.

Example 19

For the preparation of P7, the bPEI-2:MTC-C2 molar feed ratio was 1:1 and the mass feed ratio was 9.6:1. The molar ratio found by NMR for P7 was 1:1. Therefore, m=20, q=1, n'=9, k=10, and j=43 in Scheme 5 for P7.

Example 20

For the preparation of P8, the bPEI-2:MTC-C2 molar feed ratio was 1:2 and the mass feed ratio was 4.8:1. The molar ratio found by NMR for P8 was 1:1.8. Therefore, m=20, q=1, n'=8.2, k=10, and j=43 in Scheme 5 for polymer P8.

Example 21

For the preparation of P9, the bPEI-2:MTC-C2 molar feed ratio was 1:4 and the mass feed ratio was 2.8:1. The molar ratio found by NMR for P9 was 1:4.1. Therefore, m=20, q=1, n'=5.9, k=10, and j=43 in Scheme 5 for P9.

Example 22

For the preparation of P10, the bPEI-2:MTC-C2 molar feed ratio was 1:10 and the mass feed ratio was 0.96:1. The molar ratio found by NMR for polymer P10 was 1:9.9. Therefore, m=20, q=1, n'=0.1, k=10, and j=43 in Scheme 5 for polymer P10.

Modification with TMC bPEI-2 was modified with TMC according to Scheme 6 using the general procedure of Example 12 to produce branched polyamines P11 and P14. The reaction time was 1 hour. The polymers were precipitated in anhydrous ether and dried by rotary evaporation.

Scheme 6.

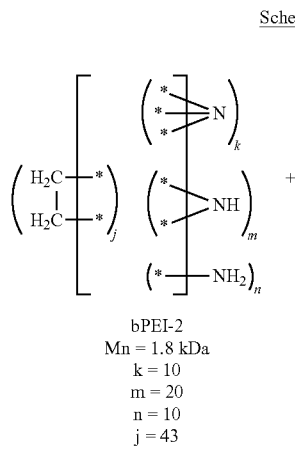

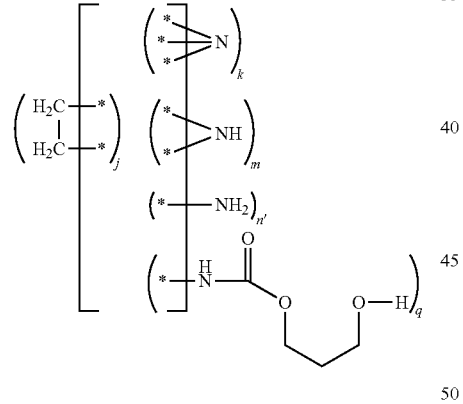

Example 23

For the preparation of P11, the bPEI-2:TMC molar feed ratio was 1:1. The molar ratio found by NMR for P11 was 1:1.2. Therefore, m=20, q=1, n'=8.8, k=10, and j=43 in Scheme 6 for P11.

Example 24

For the preparation of P14, the bPEI-2:TMC molar feed ratio was 1:4, and the mass feed ratio was 4.4:1. The molar ratio found by NMR for polymer P14 was 1:4.1. Therefore, m=20, q=4.1, n'=5.9, k=10, and j=43 in Scheme 6 for P14.

Modification with BCF bPEI-2 was modified with butyl chloroformate (BCF) according to Scheme 7 using the general procedure of Example 12 to produce branched polyamine P12. The reaction time was 1 hour.

Scheme 7.

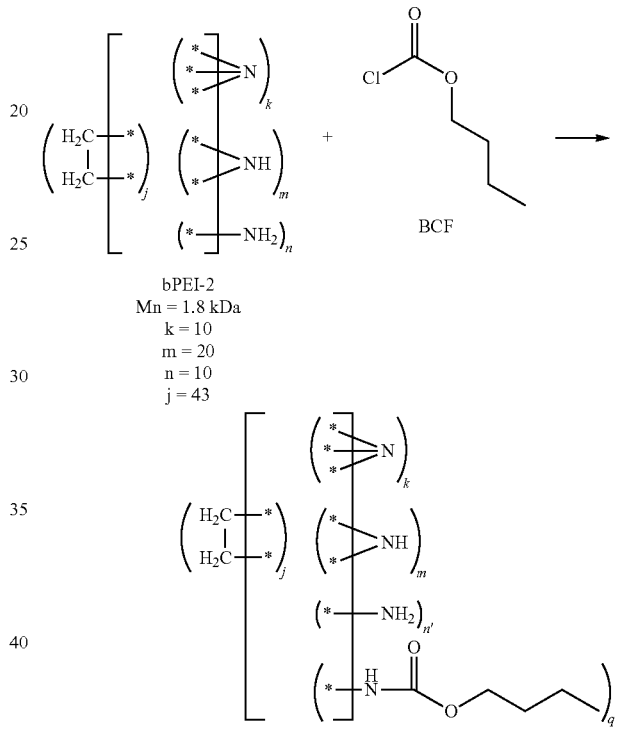

Example 25

Comparative

For the preparation of P12, the bPEI-2:BCF molar feed ratio was 1:1. The molar ratio found by NMR for polymer P12 was 1:0.9. Therefore, m=20, q=0.9, n'=9.1, k=10, and j=43 in Scheme 7 for polymer P12.

Table 4 summarizes the preparations of the polymers.

TABLE 4

| Ex. | Modified bPEI Name | Cyclic Carbonate | Cyclic Carbonate MW | Mass Feed Ratio (bPEI:Cyclic Carbonate) | Molar Feed Ratio (bPEI:Cyclic Carbonate) | Moles Cyclic Carbonate/Moles Primary Amine Groups × 100% | Used DBU? | Nitrogen Analysis (%) |
|---|---|---|---|---|---|---|---|---|
| 12 | P1 | MTC-C8 | 272 | 6.6:1 | 1:1 | 10.0 | No | 29.3 |
| 13 | P2 | MTC-C12 | 342 | 5.5:1 | 1:1 | 10.0 | No | 28.6 |

TABLE 4-continued

| Ex. | Modified bPEI Name | Cyclic Carbonate | Cyclic Carbonate MW | Mass Feed Ratio (bPEI:Cyclic Carbonate) | Molar Feed Ratio (bPEI:Cyclic Carbonate) | Moles Cyclic Carbonate/Moles Primary Amine Groups x 100% | Used DBU? | Nitrogen Analysis (%) |
|---|---|---|---|---|---|---|---|---|
| 14 | P3 | MTC-PUC2 | 322 | 5.6:1 | 1:1 | 10.0 | No | 28.2 |
| 15 | P4 | MTC-PUC8 | 406 | 4.4:1 | 1:1 | 10.0 | No | 27.2 |
| 16 | P5 | MTC-PUC12 | 463 | 3.9:1 | 1:1 | 10.0 | No | 26.5 |
| 17 | P6 | MTC-Bn | 250.25 | 7.2:1 | 1:1 | 10.0 | No | 29.2 |
| 18 | P13 | MTC-Bn | 250.25 | 1.8:1 | 1:4 | 40.0 | No | 21.4 |
| 19 | P7 | MTC-C2 | 188 | 9.6:1 | 1:1 | 10.0 | No | 30.3 |
| 20 | P8 | MTC-C2 | 188 | 4.8:1 | 1:2 | 20.0 | No | 27.5 |
| 21 | P9 | MTC-C2 | 188 | 2.4:1 | 1:4 | 40.0 | No | 23.5 |
| 22 | P10 | MTC-C2 | 188 | 0.96:1 | 1:10 | 100.00 | No | 16.3 |
| 23 | P11 | TMC | 102.1 | 18:1 | 1:1 | 10.0 | No | 31.5 |
| 24 | P14 | TMC | 102.1 | 4.4:1 | 1:4 | 40.0 | No | 27.2 |
| 25 comp | P12 | BCF | 136.6 | 13:1 | 1:1 | 10.0 | No | 30.5 |

Table 5 summarizes the NMR analysis of the modified bPEI polymers.

TABLE 5

| Ex. | Modified bPEI Name | Cyclic Carbonate | Mole Ratio Found (NMR) bPEI:Carbamate Groups[a] | % of bPEI Primary Amine Groups Modified (NMR)[b] | # of bPEI Primary Amine Groups Modified Per Mole bPEI[a,c] |
|---|---|---|---|---|---|
| 12 | P1 | MTC-C8 | 1:1 | 10.0 | 1 |
| 13 | P2 | MTC-C12 | 1:0.9 | 9.0 | 0.9 |
| 14 | P3 | MTC-PUC2 | 1:0.9 | 9.0 | 0.9 |
| 15 | P4 | MTC-PUC8 | 1:0.9 | 9.0 | 0.9 |
| 16 | P5 | MTC-PUC12 | 1:1 | 10.0 | 1 |
| 17 | P6 | MTC-Bn | 1:1.1 | 11.0 | 1.1 |
| 18 | P13 | MTC-Bn | 1:4.7 | 47.0 | 4.7 |
| 19 | P7 | MTC-C2 | 1:1 | 10.0 | 1 |
| 20 | P8 | MTC-C2 | 1:1.8 | 18.0 | 1.8 |
| 21 | P9 | MTC-C2 | 1:4.1 | 41.0 | 4.1 |
| 22 | P10 | MTC-C2 | 1.9.9 | 99.0 | 9.9 |
| 23 | P11 | TMC | 1:1.2 | 12.0 | 1.2 |
| 24 | P14 | TMC | 1:4.1 | 41.0 | 4.1 |
| 25 comp | P12 | BCF | 1:0.9 | 9.0 | 0.9 |

[a]based on 1 mole bPEI-2 = 1800 g and 10 primary amine groups per mole.
[b]A value greater than 100% indicates reaction at all active primary amine sites, and reaction of secondary amine groups and/or ring opening polymerization of the cyclic carbonate monomer.
[c]a number greater than 10 in Examples 31-37, indicates reaction at all active primary amine sites, and reaction of secondary amine groups and/or ring opening polymerization of the cyclic carbonate monomer.

III. Complexes with Biologically Active Materials

Cell Cultures.

HepG2 and SK-OV-3 cells were cultured in Minimum Essential Medium Eagle (MEM, Invitrogen, Singapore, for HepG2) and RPMI 1640 medium (Invitrogen, Singapore, for SK-OV-3). Both media were supplemented with 10% fetal bovine serum (FBS, Invitrogen, Singapore), streptomycin at 100 microgram/mL, penicillin at 100 U/mL, L-glutamine at 2 mM, and 1 mM sodium pyruvate (Sigma-Aldrich, Singapore). MEM was further supplemented with 1 mM non-essential amino acids (Sigma-Aldrich, Singapore). Cells were cultured at 37° C., under an atmosphere of 5% $CO_2$ and 95% humidified air. All cell lines were split using Trypsin/EDTA medium when 90% confluence was reached.

Formation of DNA Complexes.

Modified bPEI-2 polymer was dissolved in DNase/RNase-free water and HPLC water respectively to make an aqueous polymer solution. To form the complex, an equal volume solution of DNA (GFP reporter gene or luciferase reporter gene) was dripped into the polymer solution to achieve the intended N/P ratios (molar ratio of nitrogen content in the polymer to the phosphorus content of the nucleic acids) under gentle vortexing for about 10 seconds. The mixture was equilibrated at room temperature for 30 minutes to allow for complete electrostatic interaction between the polymer and the DNA molecules, before being used for subsequent studies. Control complexes of non-modified bPEI-2 and non-modified bPEI-25 were prepared similarly.

Particle Size and Zeta Potential Analysis of DNA Complexes.

The particle sizes and zeta potentials of the post-equilibrated polymer/DNA complexes were measured by dynamic light scattering (Brookhaven Instrument Corp., Holtsville, N.Y., U.S.A.) using a He—Ne laser beam at 658 nm, with a scattering angle of 90° and Zetasizer (Malvern Instrument Ltd., Worcestershire, UK) respectively. Particle size and zeta potential measurements were repeated for 3 runs per sample and reported as the mean±standard deviation of 3 readings.

Table 6 lists the hydrodynamic radius of some of the modified bPEI-2 polymers at different N/P ratios.

TABLE 6

| Ex. | Name | Cyclic Carbonate Monomer | % of Primary Amine Groups (NMR)[a] | Hydrodynamic Radius, $R_h$, of DNA complex Modified (nm) | | | |
|---|---|---|---|---|---|---|---|
| | | | | N/P 10 | N/P 20 | N/P 30 | N/P 40 |
| 12 | P1 | MTC-C8 | 10.0 | 96.7 | 97.9 | 102.2 | 103.9 |
| 13 | P2 | MTC-C12 | 9.0 | 96.6 | 92.5 | 94.3 | 92.9 |
| 14 | P3 | MTC-PUC2 | 9.0 | 99.9 | 99.3 | 107.9 | 108.8 |
| 15 | P4 | MTC-PUC8 | 9.0 | 104.6 | 102.1 | 99.8 | 102.6 |
| 16 | P5 | MTC-PUC12 | 10.0 | 102.8 | 105.5 | 110.6 | 110.6 |
| 17 | P6 | MTC-Bn | 11.0 | 105.5 | 100.9 | 103.5 | 99.9 |
| 18 | P13 | MTC-Bn | 47.0 | 132.8 | 124.6 | 118.1 | 130.3 |
| 19 | P7 | MTC-C2 | 10.0 | 97.8 | 96.9 | 96.5 | 104.4 |
| 20 | P8 | MTC-C2 | 20.0 | 111 | 109.5 | 106.6 | 105.4 |
| 21 | P9 | MTC-C2 | 40.0 | 108.2 | 105.8 | 108.4 | 106.6 |
| 22 | P10 | MTC-C2 | 100.0 | 135.8 | 121.6 | 122.1 | 125.4 |
| 23 | P11 | TMC | 10.0 | 98.4 | 101.4 | 119 | 165.8 |
| 24 | P14 | TMC | 41.0 | | | | |
| 25 (comp) | P12 | BCF | 10.0 | 108.9 | 101.3 | 106 | 00.9 |

[b]A percentage greater than 100 indicates reaction of all active primary amine sites, and reaction of secondary amine groups and/or ring opening polymerization of the cyclic carbonate monomer.

Polymeric nanoparticles, typically in the size range of 20 nm to 200 nm, are sufficiently large to avoid premature elimination via glomerular filtration in the kidneys, but are small enough to enter blood vessels and to capitalize on the enhanced permeation and retention (EPR) effect for passive accumulation in the target tumor tissues. As can be seen from FIG. 1 the luciferase reporter gene complexes of the modified bPEI-2 polymers had an average particle size of about 100 nm, whereas the luciferase reporter gene complex of non-modified bPEI-2 prepared at N/P 40 has a particle size of about 3000 nm.

Figure 2:
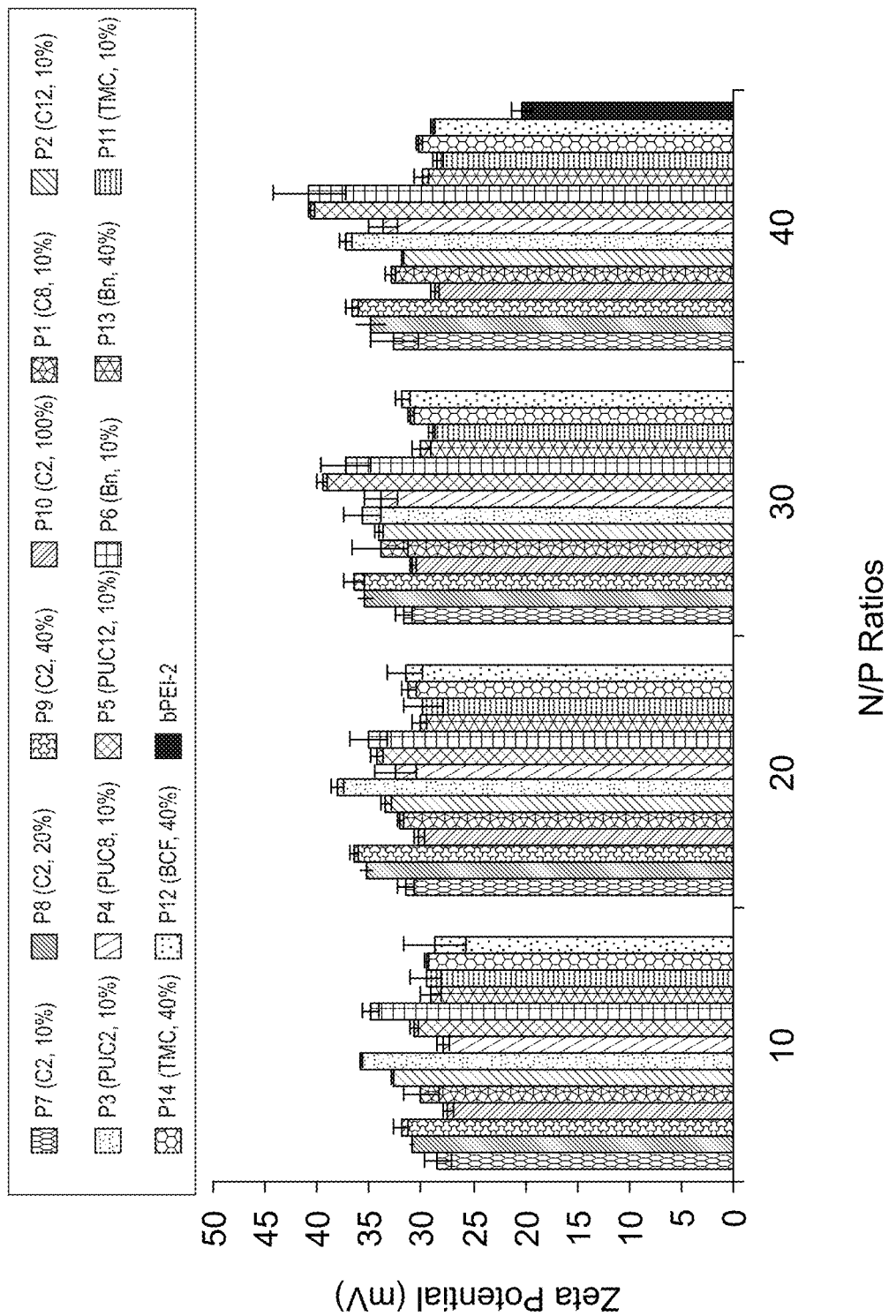
FIG. 2 is a bar graph showing zeta potentials of polymer/DNA complexes prepared with luciferase reporter gene and various modified bPEI-2 polymers. The cyclic carbonate monomer used to form the modified bPEI-2 polymer is shown in parentheses. The complexes were prepared at N/P ratios of 10 to 40. A DNA complex of non-modified bPEI-2 was prepared at N/P ratio of 40 as a control.

Hydrophobic modifications of bPEI-2 caused a significant increase in zeta potential compared to the non-modified bPEI-2 control complex (FIG. 2). Without being bound by theory, this might aid nanoparticle interaction with the negative charged cell membranes and thus enhance endocytosis and transfection.

Gel Retardation Assay.

Various formulations of polymer/luciferase reporter gene complexes were prepared as described above with N/P ratios in a range of 1 to 10 or 1 to 15. Post equilibration, the complexes derived from bPEI-2 were electroporated on 0.7% agarose gel, and the complex formed with bPEI-25 was electroporated on 1% agarose gel. The agarose gel was stained with 5 microliters of 10 mg/mL ethidium bromide per 50 mL of agarose solution. The gel was run in 0.5×TBE buffer at 80 V for 50 min, and then analyzed under a UV illuminator (Chemi Genius, Evolve, Singapore) to reveal the relative position of the complexed DNA to the naked DNA plasmid.

Figure 3:
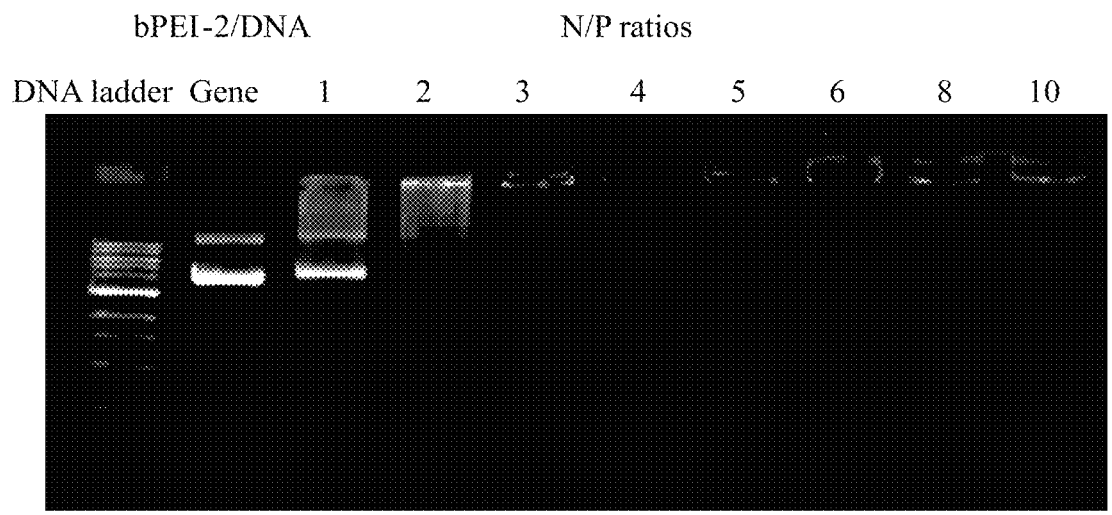
FIG. 3 is a photograph of a DNA ladder obtained for a control polymer/DNA complex prepared with luciferase reporter gene and non-modified bPEI-2.
Figure 4:
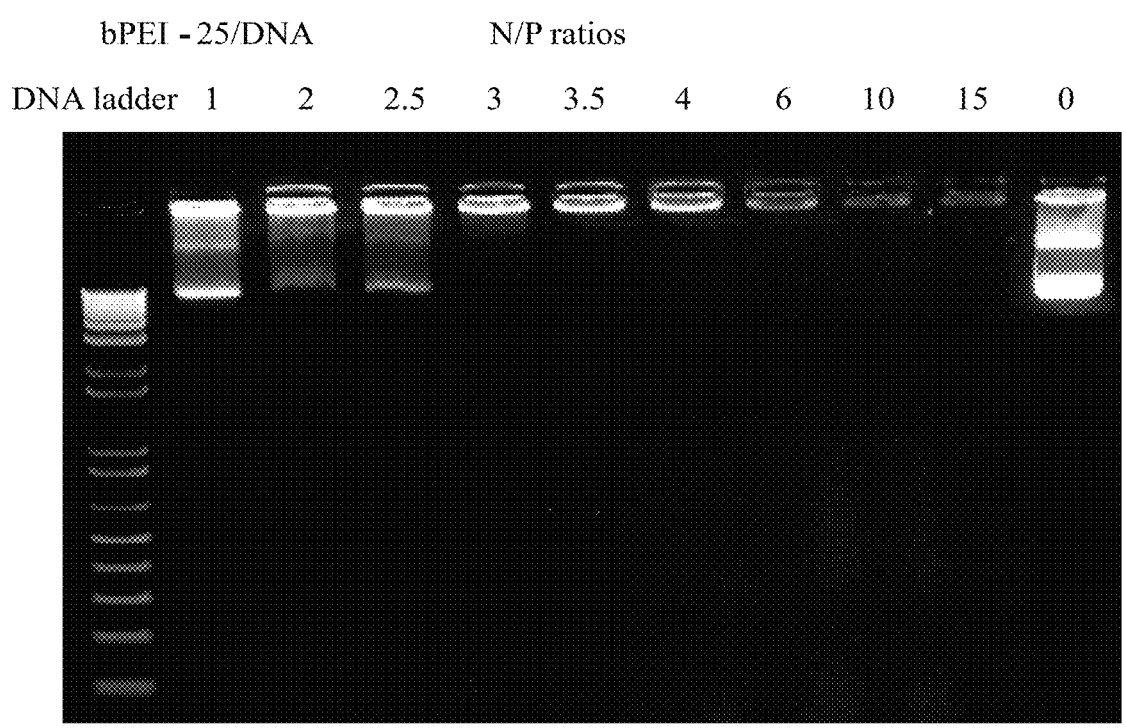
FIG. 4 is a photograph of a DNA ladder obtained for a control polymer/DNA complex prepared with luciferase reporter gene and non-modified bPEI-25 (number average molecular weight (Mn)=10000 kDa, weight average molecular weight (Mw)=25000).
Figure 5:
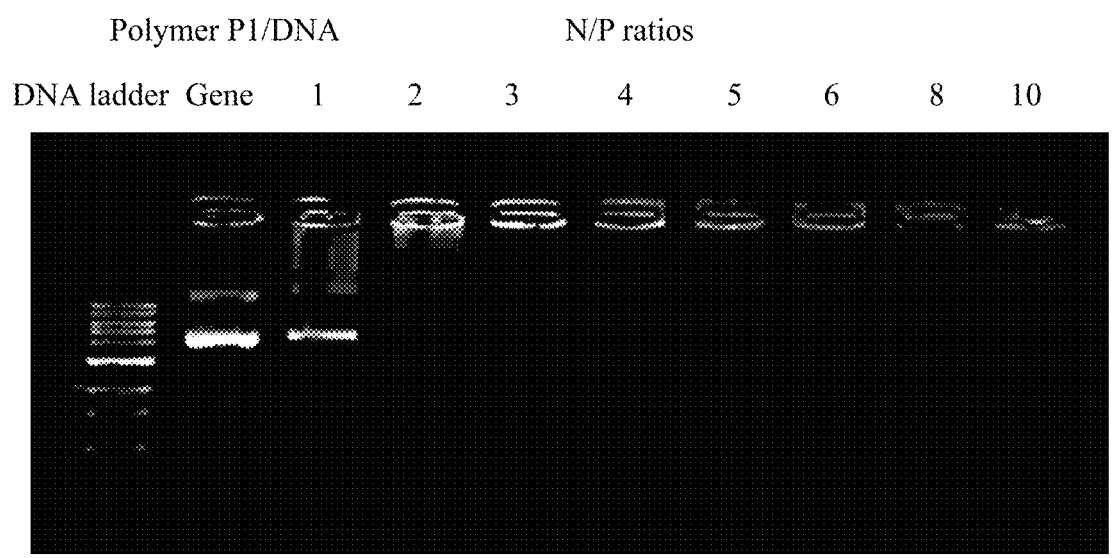
FIGS. 5-11 are photographs of DNA ladders for selected polymer/DNA complexes prepared with luciferase reporter gene and various modified bPEI-2 polymers.
Figure 6:
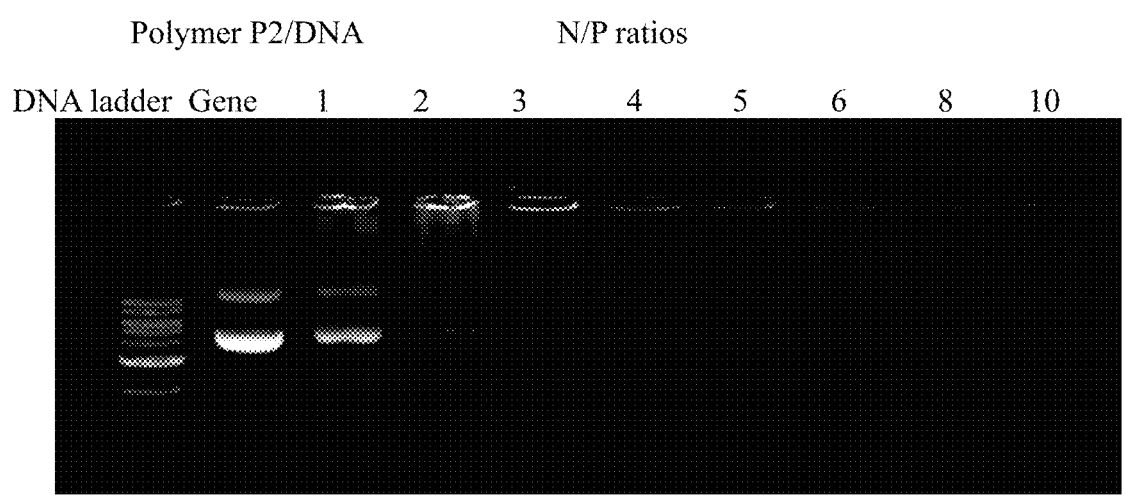
Figure 7:
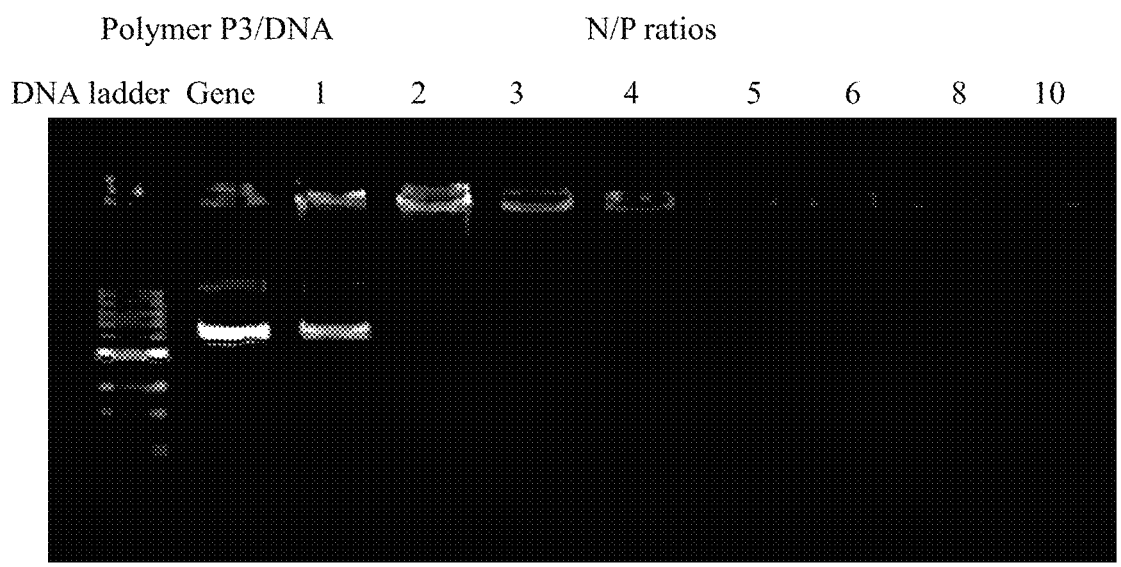
Figure 8:
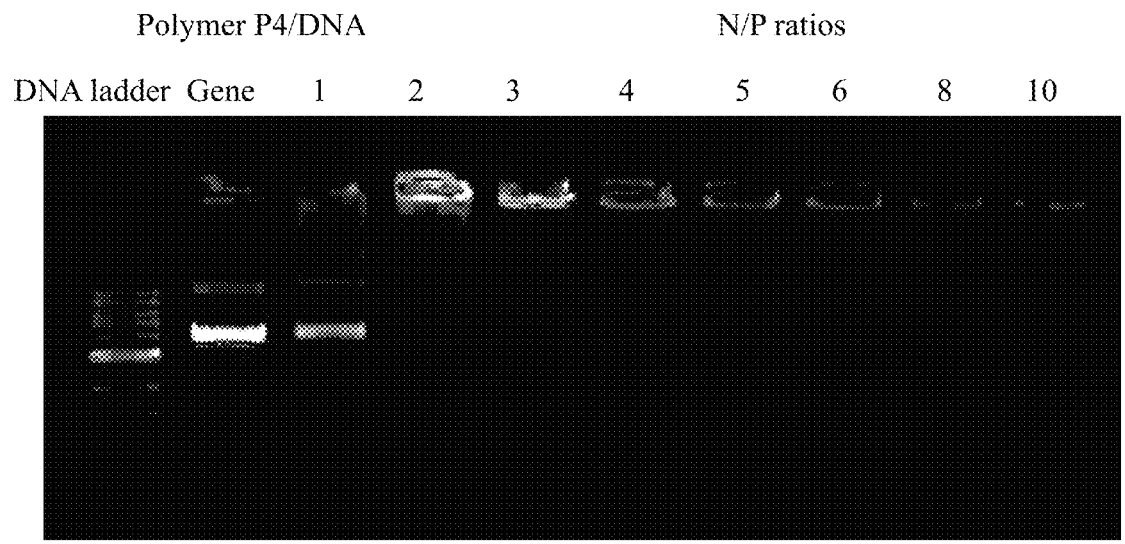
Figure 9:
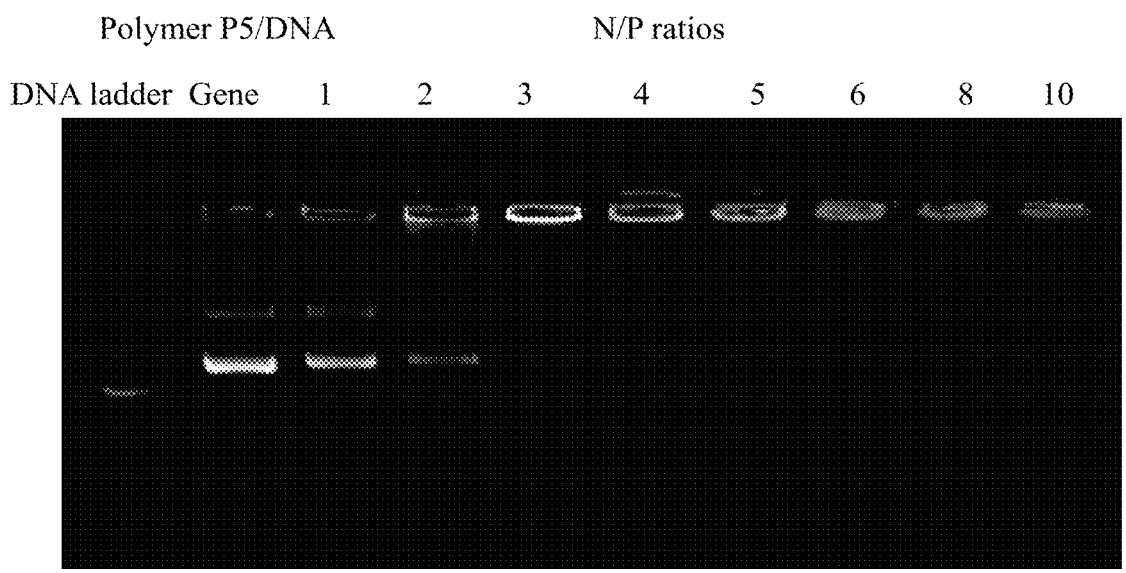
Figure 10:
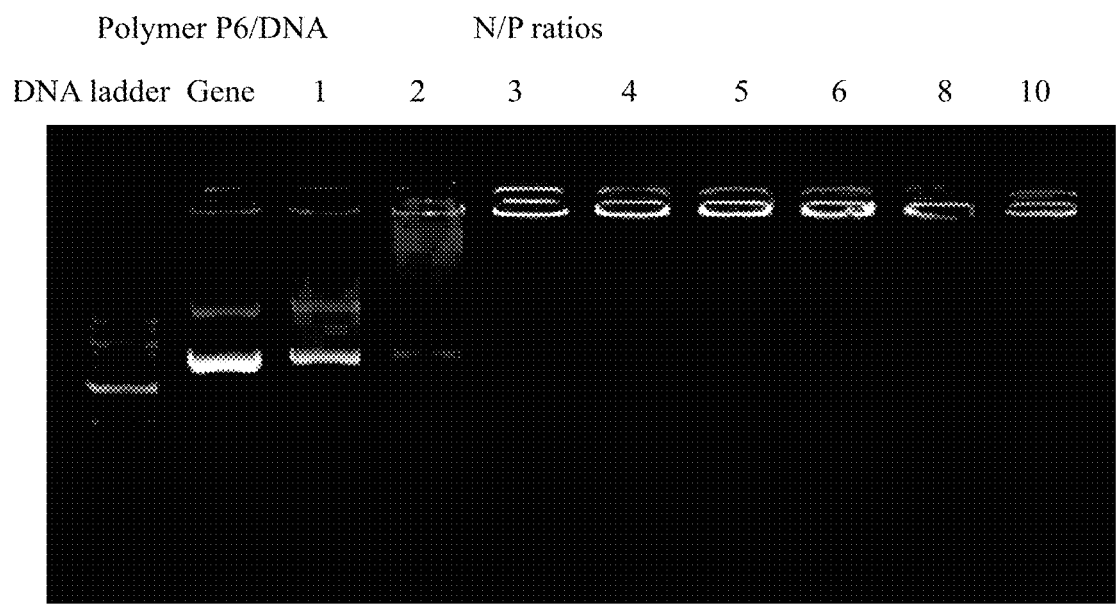
Figure 11:
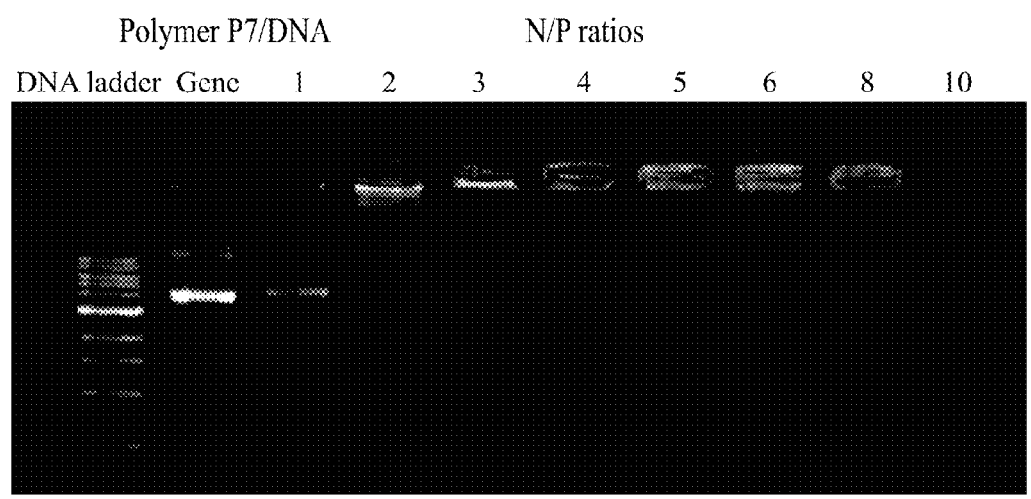

Polymers P1 to P7 were able to condense DNA as effectively at N/P 3 (FIGS. 5 to 11, respectively) as the non-modified bPEI-2 (FIG. 3) and non-modified bPEI-25 (FIG. 4).

Buffering Capacity of MTC-C2 Modified bPEI-2.

P7, P8, P9, and P10 represent an MTC-C2 modification level series of bPEI-2 (10%, 20%, 40% and 100% modification of the primary amine groups, respectively). The buffering capacities of these polymers and non-modified bPEI-2 are shown in Table 7. The buffering capacity was determined over a pH range of 2 to 11. The polymer (0.1 mmol nitrogen atoms) was first dissolved in 5 mL of NaCl solution (150 mM). 15 mL of 0.01HCl was added to bring the pH down to 2 and the solution was then titrated against 0.01M NaOH using the auto-titrator (Spectralab Instruments). The buffering capacity is defined as the percentage of amine groups protonated over a pH of 5.1 to 7.4 and is calculated by the following equation:

Buffering capacity(%)=100×($\Delta V_{NaOH}$×0.01 M)/N mol where $\Delta V_{NaOH}$ is the volume of NaOH (0.01 M) required to increase the pH from 5.1 to 7.4, and N mol is the total moles of protonatable amines.

TABLE 7

| Polymer | Buffering Capacity (%) |
|---|---|
| bPEI-2 | 21.9 |
| P7 | 21.2 |
| P8 | 22.4 |
| P9 | 21.2 |
| P10 | 20.3 |

Figure 12:
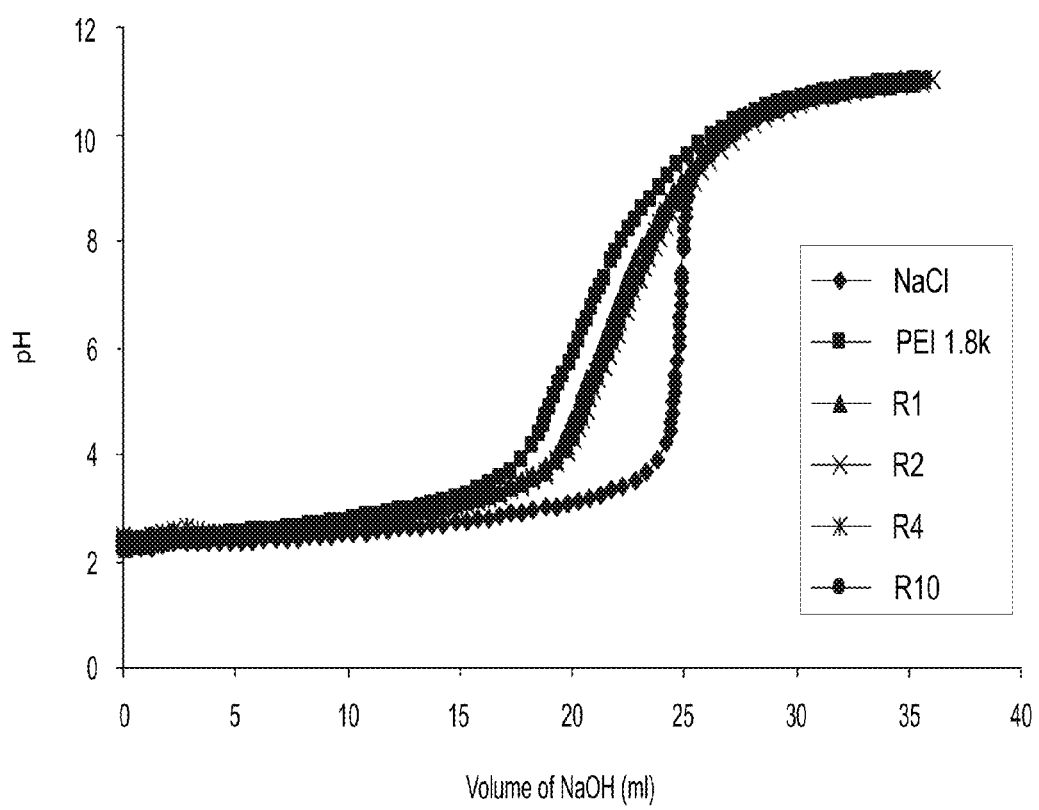
FIG. 12 is a graph comparing the buffering capacity of several modified bPEI-2 polymers prepared with MTC-C2. Buffering capacity decreased with increasing content of MTC-C2.

FIG. 12 is a graph plotting pH as a function of NaOH added. The data indicate that increasing the amount of MTC-C2 substitution leads to decreased buffering capacity.

Figure 13:
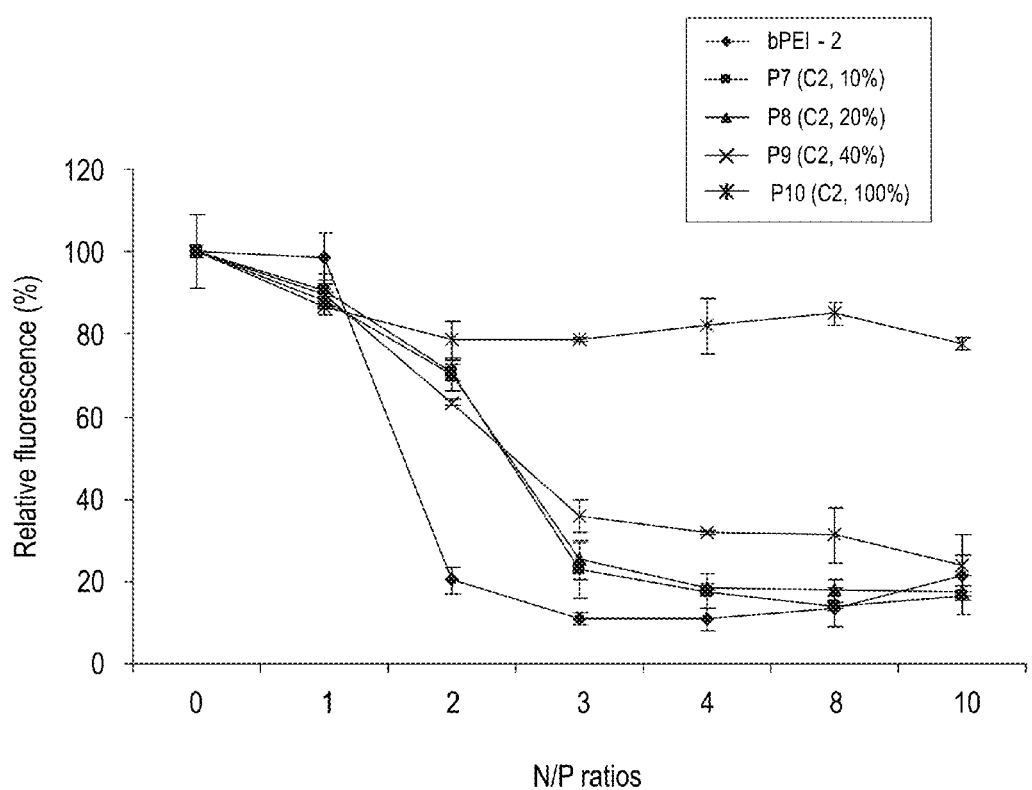
FIG. 13 is a graph comparing binding capacity of selected modified bPEI-2 polymers prepared with MTC-C2 to luciferase reporter gene. DNA binding capacity decreased with increasing content of MTC-C2.

FIG. 13 is a graph comparing the luciferase reporter gene binding capability of P7, P8, P9, P10, and non-modified bPEI-2 measured as relative % fluorescence of the free gene at N/P 0 to 10. Increasing the degree of MTC-C2 substitution produced weaker DNA binding efficiency especially in P10, which has approximately 100% of the primary amine groups modified.

Luciferase Gene Expression.

The in vitro transfection efficiency of complexes prepared with modified bPEI-2 polymer and luciferase reporter gene was investigated using HepG2 and SK-OV-3 cell lines. HepG2 cells were seeded onto 24-well plates at a density of 8×10⁴ cells per 500 microliters per well for luciferase gene delivery. SK-OV-3 cells were seeded onto 24 well plates at a density of 8×10⁴ cells per 500 microliters per well for luciferase gene delivery. After 24 hours, the plating media were replaced with fresh growth media, followed by the dropwise addition of 50 microliters of complex solution containing 2.5 micrograms luciferase plasmid DNA at various N/P ratios. Following 4 hours of incubation, free complexes were removed by replacing the medium in each well. After a further 68 hours of incubation, the cell culture medium in each well was removed and the cells rinsed once with 0.5 mL of phosphate-buffered saline (PBS, pH 7.4). For luciferase expression assay, 0.2 mL of reporter lysis buffer was added to each well. The cell lysate collected after two cycles of freezing (−80° C., 30 min) and thawing was cleared by centrifugation at 14000 rpm for 5 min, after which, 20 microliters of supernatant was mixed with 100 microliters of luciferase substrate for the determination of relative light units (RLU) using a luminometer (Lumat LB9507, Berthold, Germany). The RLU readings were normalized against the protein concentration of the supernatant determined using the BCA protein assay to give the overall luciferase expression efficiency. In all in vitro gene expression experiments, naked DNA was used as a negative control. Non-modified bPEI-2/DNA complex and non-modified bPEI-25/DNA complex were used as positive controls. These controls were prepared at the optimal N/P ratio (i.e., N/P 40 for non-modified bPEI-2, N/P 10 for non-modified bPEI-25), which induced high gene expression efficiency yet provided close to or more than 50% cell viabil ity. Data were expressed as mean±standard deviations of four replicates.

Luciferase Expression Results.

Figure 14:
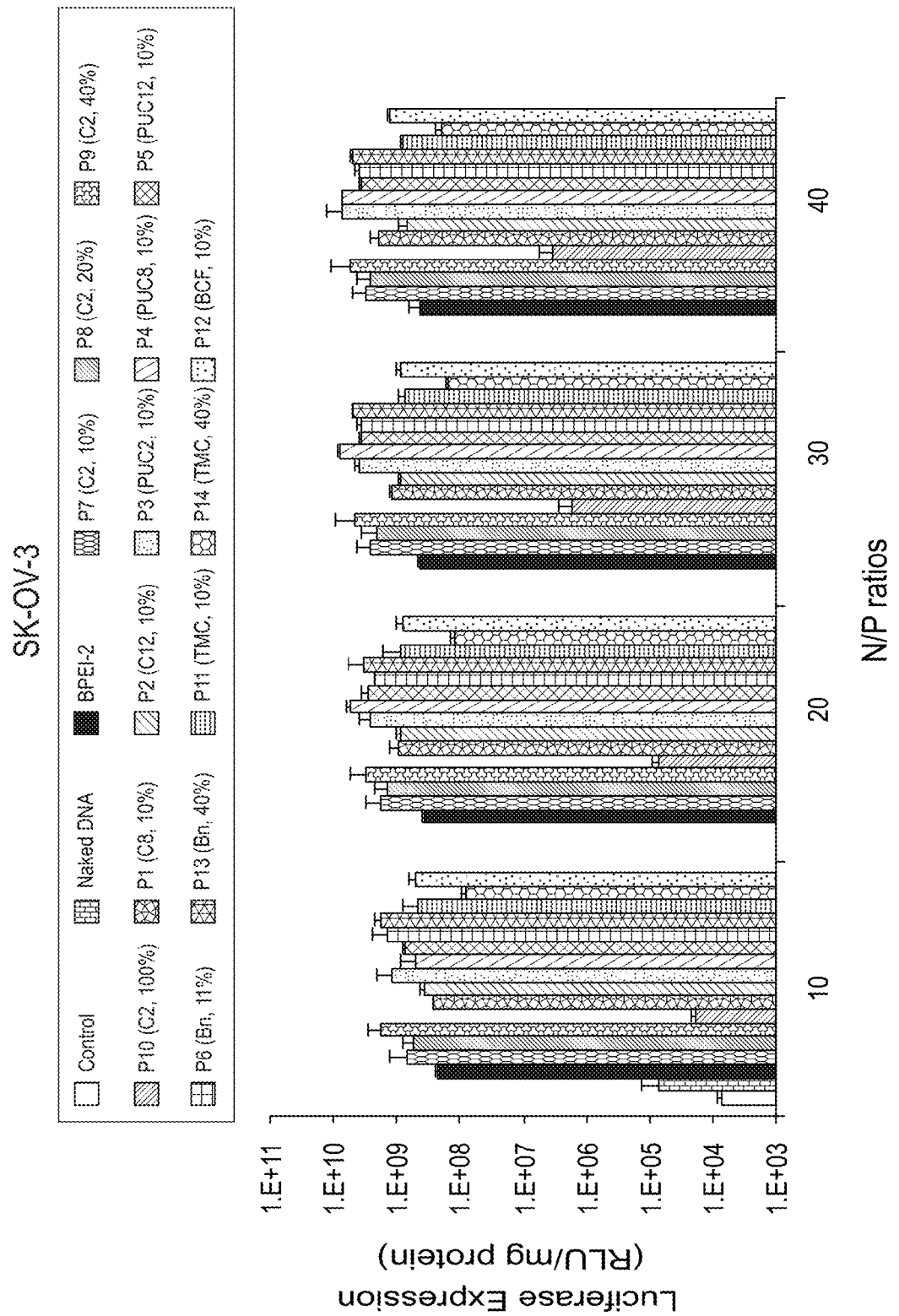
FIG. 14 is a bar graph showing the luciferase expression level mediated by various modified bPEI-2 polymer/DNA complexes in SK-OV-3 cells at different N/P ratios. The cyclic carbonate monomer used to form the modified bPEI-2 polymer is shown in parentheses. Controls include a DNA complex of non-modified bPEI-2 at N/P 40, DNA alone, and no DNA (Labeled "0" on the chart). Results represent mean±standard deviation of triplicates. Luciferase expression level increased with MTC-C2 modification levels from 10% to 40% of the primary amine groups of non-modified bPEI-2. 100% modification of the primary amine groups with MTC-C2 resulted in lower expression levels compared to non-modified bPEI-2.

FIG. 14 is a bar chart comparing the luciferase expression level in SK-OV-3 cells mediated by the luciferase reporter gene complexes of selected modified bPEI-2 polymers at N/P 10 to 40. Comparing P7 to P10 (modification levels at 10%, 20%, 40% and 100% of the primary amine groups of bPEI-2 using MTC-C2), the luciferase expression level of the modified bPEI-2 polymers exceeded that of the non-modified bPEI-2 control at each level except 100% (P10), where the expression level was 2 to 4 orders of magnitude less than the non-modified bPEI-2 control. Chain length of the alkyl ester at a modification level of 10% had little effect on expression level (compare P7, P1, and P2 having ethyl, octyl, and dodecyl ester groups, respectively). Increasing the modification level using MTC-C2 (ethyl ester) from 10% to 100% (P7 to P10) resulted in sharp decline in luciferase expression level above 40% modification. The addition of a phenylurea group (P3, P4 and P5) to the end of the ester chain enhanced luciferase expression levels compared to the non-urea counterparts (P7, P1 and P2). P3 and P4 achieved the highest expression level of about $10^{9.5}$ RLU/mg protein at N/P 40, which is about 10-fold higher than the expression level obtained for the control non-modified bPEI-2 complex. MTC-Bn modified bPEI-2 at 10% and 40% modification levels (P6 and P13, respectively) also had high luciferase expression levels. On the other hand, TMC modified bPEI-2 at 10% and 40% modification levels (P11 and P14, respectively) had expression levels comparable to or lower than the non-modified bPEI-2. Butylchloroformate (BCF) modified bPEI-2 at 10% modification level (P12) also had lower luciferase expression levels in general compared to the cyclic carbonate modified bPEI-2 polymers.

Summarizing, in general, modifications with cyclic carbonate produced higher expression levels than modification with a non-cyclic carbonate butylchloroformate. Modification levels of 10% to 50%, more particularly of 10% to 40%, were favored over 100% modification level using the cyclic carbonates. In some instances, expression levels exceeded the non-modified bPEI-2 by more than an order of magnitude.

Figure 15:
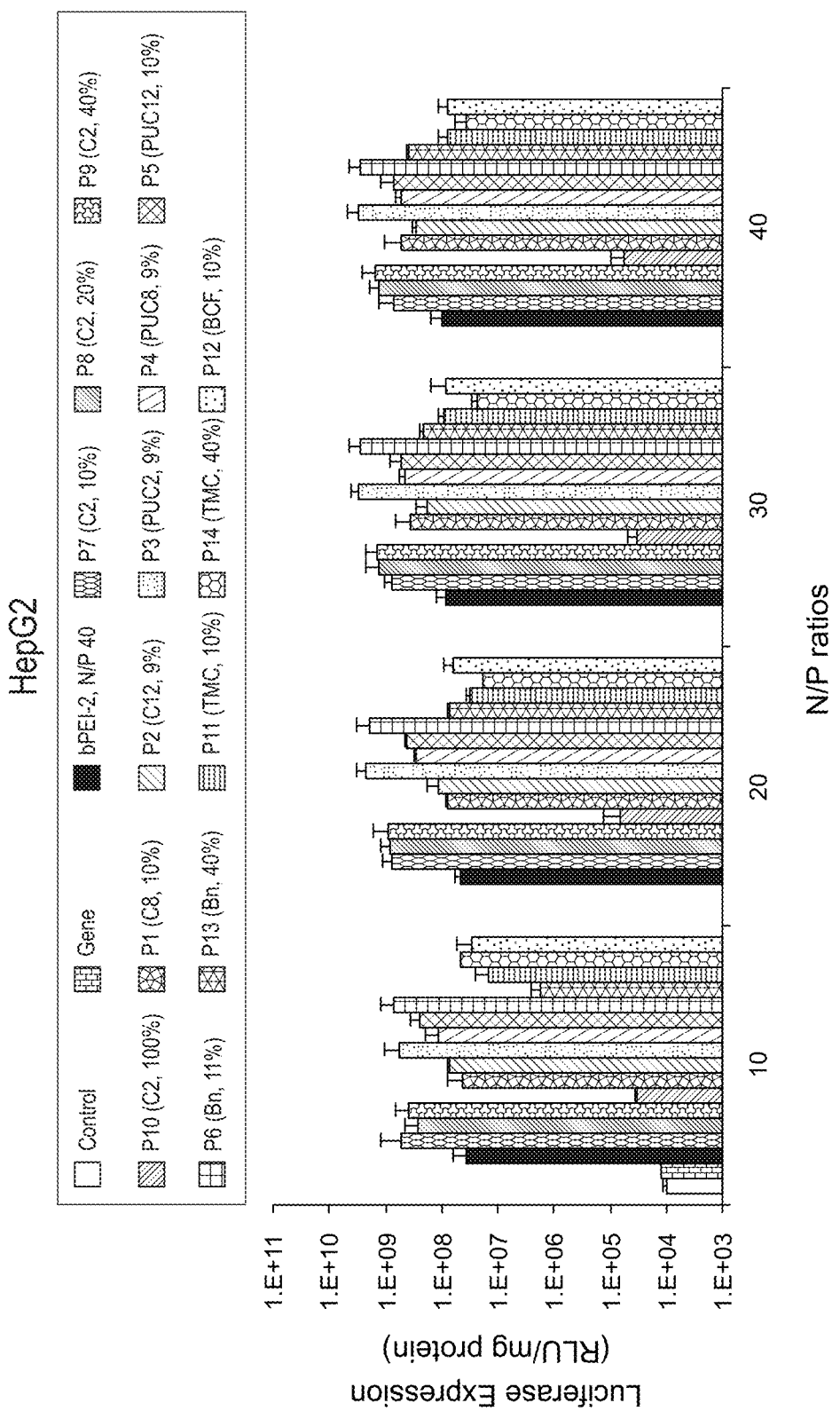
FIG. 15 is a bar graph showing the luciferase expression level mediated by various modified bPEI-2 polymer/DNA complexes in HepG2 cells at different N/P ratios.

A similar trend was observed in the HepG2 cell line (FIG. 15). In this cell line, P7, P8, P9, P3, and P6 were especially favored, achieving about 1-1.5 orders of magnitude higher luciferase expression levels compared to non-modified bPEI-2. An MTC-C2 modification level higher than about 40% of the primary amine groups resulted in lower luciferase expression level.

Cytotoxicity Test.

The cytotoxicity of the polymer/DNA complexes was studied using the standard MTT assay protocol on SK-OV-3 and HepG2 cells. The luciferase plasmid was used for complex formation and treatment of both cell lines.

HepG2 and SK-OV-3 cells were seeded onto 96-well plates at densities of 10000 cells, 5000 and 16000 cells per well, respectively, and allowed to grow to 60% to 70% confluency before treatment. Polymer/DNA or polymer/siRNA complexes at various N/P ratios were prepared in water as described above. The cells in each well were then incubated with growth medium comprising of 10 microliters of polymer/nucleic acid complexes and 100 microliters of fresh medium for 4 hours at 37° C. Following incubation, the medium was replaced with fresh growth medium and incubated further for 68 hours. Subsequently, 100 microliters of growth medium and 20 microliters of MTT solution (5 mg/mL in PBS) were then added to each well and the cells were incubated for 4 hours at 37° C. Formazan crystals formed in each well were solubilized using 150 microliters of DMSO upon removal of growth media. A 100 microliter aliquot from each well was then transferred to a new 96-well plate for determination of absorbance using a microplate spectrophotometer at wavelengths of 550 nm and 690 nm. Relative cell viability was expressed as $[(A_{550}-A_{690})$sample/$(A_{550}-A_{690})$control]×100%. Data were expressed as mean±standard deviations of at least eight replicates per N/P ratio.

Cytotoxicity Results.

Figure 16:
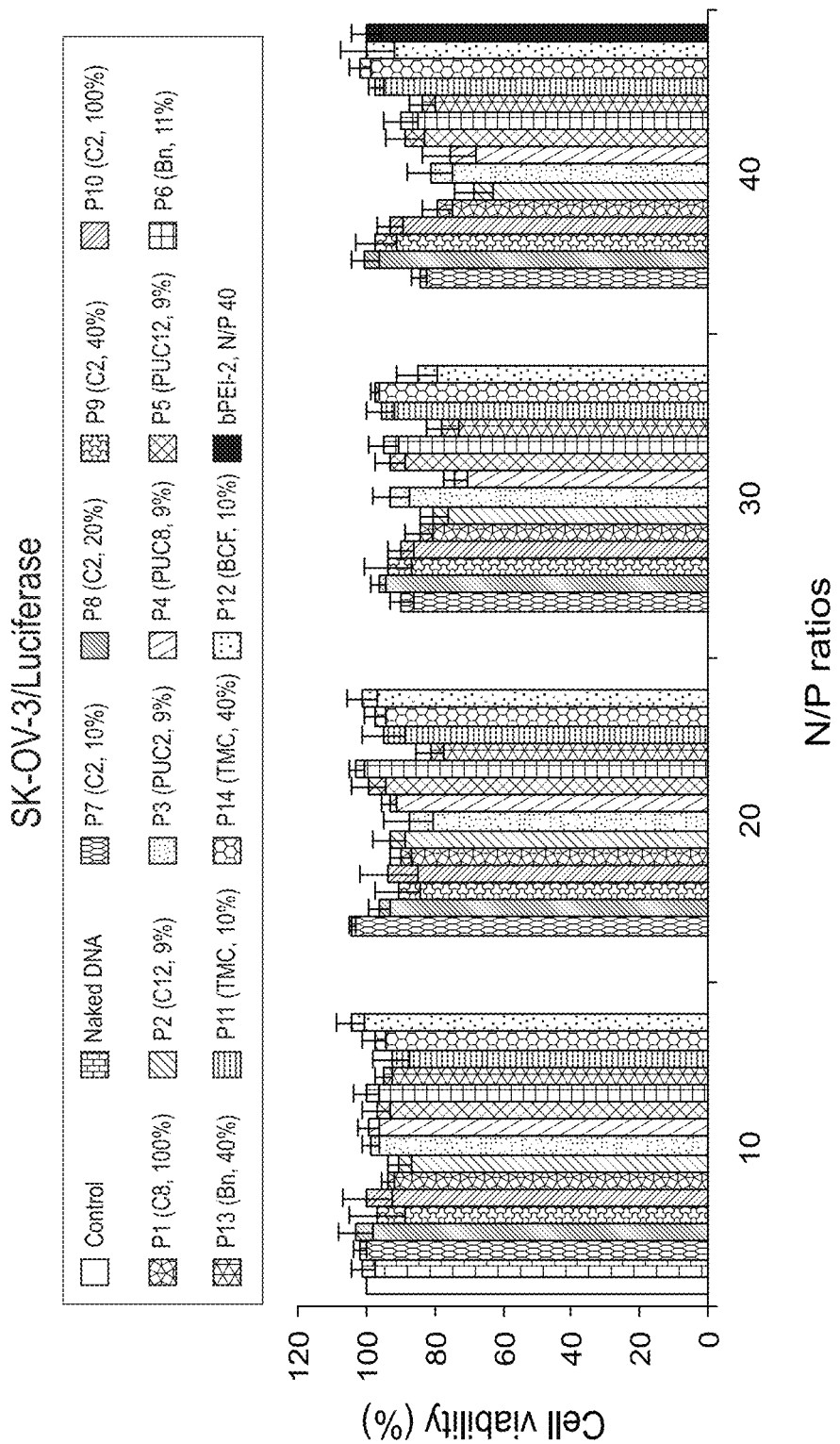
FIG. 16 is a bar graph showing the cell viability of SK-OV-3 cells after incubation with various modified bPEI-2 polymer/luciferase complexes prepared at N/P 10 to 40.

FIG. 16 is a bar graph showing the viability of SK-OV-3 cells after incubation with various luciferase reporter gene complexes of modified bPEI-2 polymers at N/P ratios 10 to 40. Cell viability for the non-modified bPEI-2 polymer alone at N/P 40 is also shown. Generally, within a given cyclic carbonate series, increasing the N/P ratio increased the cytotoxicity of each modified bPEI-2 polymer complex. Nonetheless, the SK– OV-3 cell viability remained above about 80% for each branched polyamine except P2 (10% modification level using MTC-C12) and P4 (10% modification level using MTC-PUC8).

Figure 17:
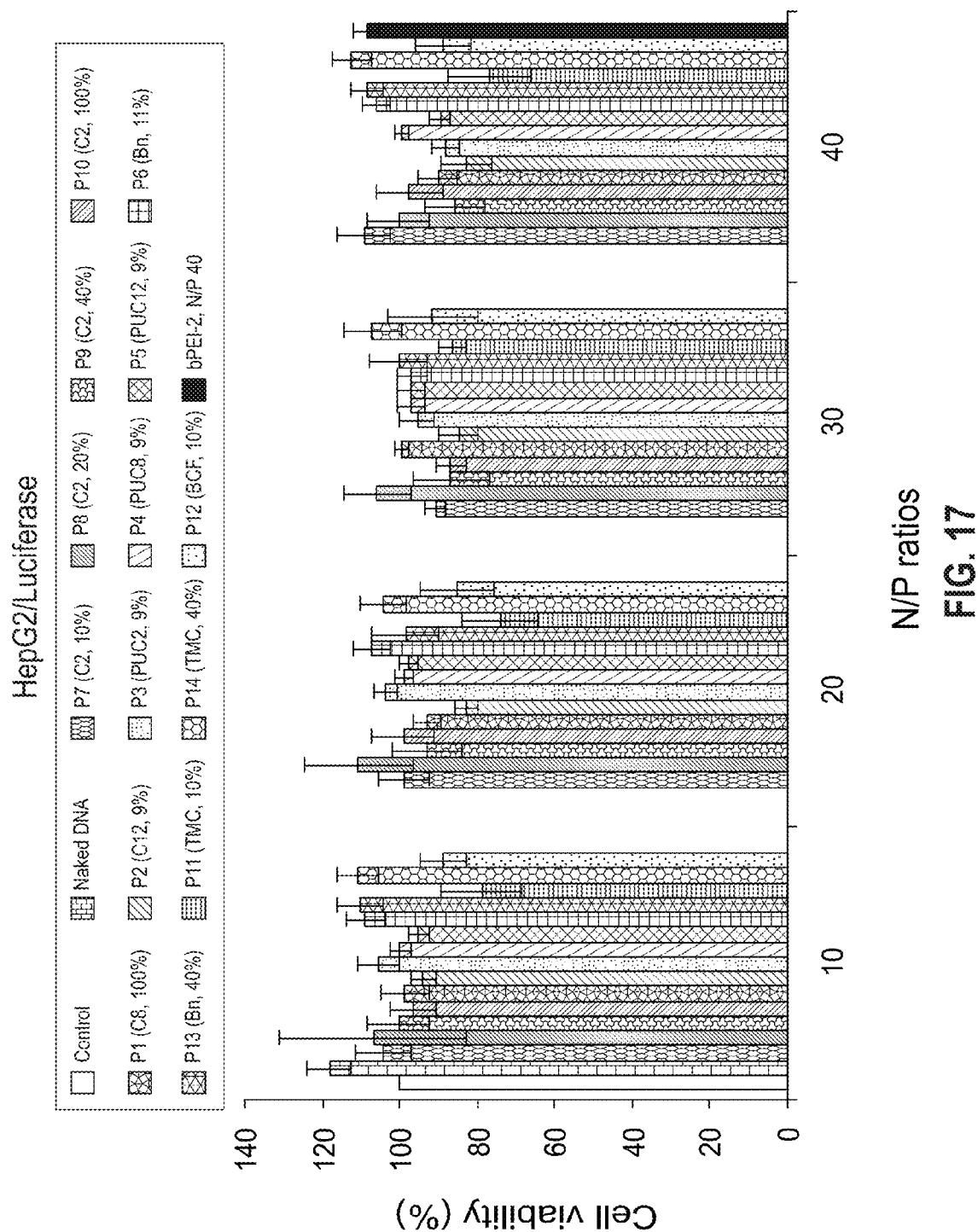
FIG. 17 is a bar graph showing the cell viability of HepG2 cells after incubation with various modified bPEI-2 polymer/luciferase complexes prepared at N/P 10 to 40.

FIG. 17 is a bar graph showing the viability of HepG2 cells after incubation with various luciferase reporter gene complexes of modified bPEI-2 polymers at N/P ratios 10 to 40. Cell viability for the non-modified bPEI-2 polymer alone at N/P 40 is also shown. As with SK-OV-3 cells above, within a given cyclic carbonate series, increasing the N/P ratio increased the cytotoxicity of each modified bPEI-2 polymer complex. Here, the SK-OV-3 cell viability remained above about 80% at N/P 10 to 40 for each polymer except P11 (10% modification level with TMC).

GFP Transfection Efficiency.

The in vitro gene transfection efficiency of green fluorescence protein (GFP) reporter gene was investigated using SK-OV-3 cells and HepG2 cells. SK-OV-3 cells and HepG2 cells were seeded onto 24 well plates at a density of $8 \times 10^4$ cells per 500 microliters per well for GFP gene delivery. After 24 hours, the plating media were replaced with fresh growth media, followed by the drop-wise addition of 100 microliters of complex solution (containing 3.5 micrograms GFP plasmid DNA) at various N/P ratios. Following 4 hours of incubation, free complexes were removed by replacing the medium in each well. After a further 68 hours of incubation, the cell culture medium in each well was removed and the cells rinsed once with 0.5 mL of phosphate-buffered saline (PBS, pH 7.4).

For GFP protein expression analysis, 0.3 mL trypsin was added to detach cells in each well. Fresh growth medium (0.3 mL) was then added, and the cell suspension was centrifuged at 1500 rpm for 5 min. Two further cell-washing cycles of re-suspension and centrifugation were carried out in FACS buffer (PBS supplemented with 2% bovine serum albumin). The percentage of cells expressing GFP was then determined using a flow cytometer (FACSCalibur, BD Biosciences, USA) from 10000 events, and reported as mean±standard deviations of triplicates.

Figure 18:
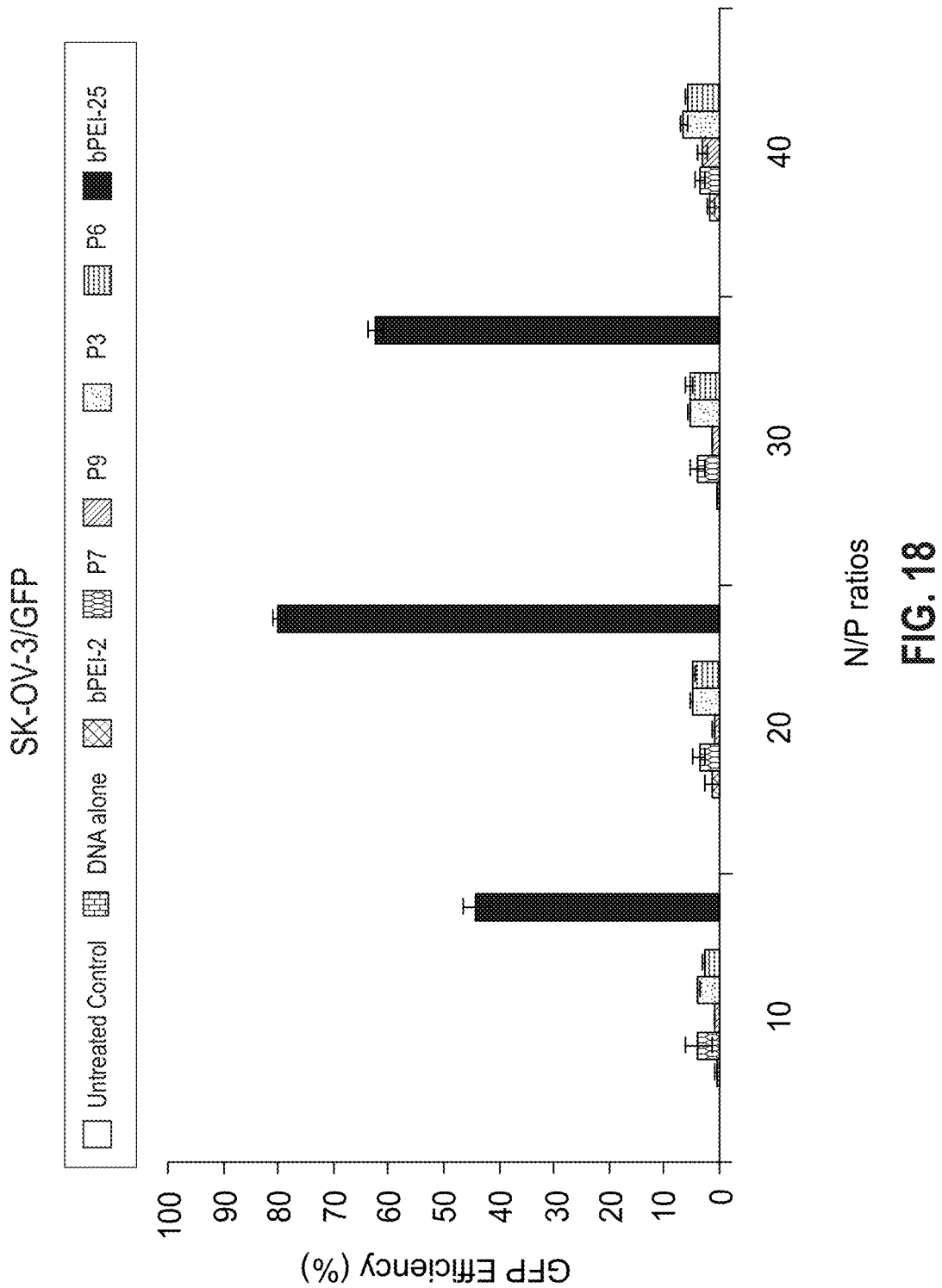
FIG. 18 is a bar graph comparing the in vitro GFP gene transfection efficiency in SK-OV-3 cells of modified bPEI-25 polymers P3, P6, P7, and P9 at various N/P ratios.

FIG. 18 is a bar graph comparing the in vitro GFP gene transfection efficiency in SK-OV-3 cells of modified bPEI-2 polymers P3, P6, P7, and P9 at various N/P ratios. Controls included untreated cells, GFP gene alone, non-modified bPEI-2, and non-modified bPEI-25. Non-modified bPEI-2 had a peak efficiency of about 1.7% at N/P 40, while non-modified bPEI-25 had a peak efficiency of about 80% at N/P 20. P3 and P6 had peak efficiencies of about 6.2% at N/P 40.

Figure 19:
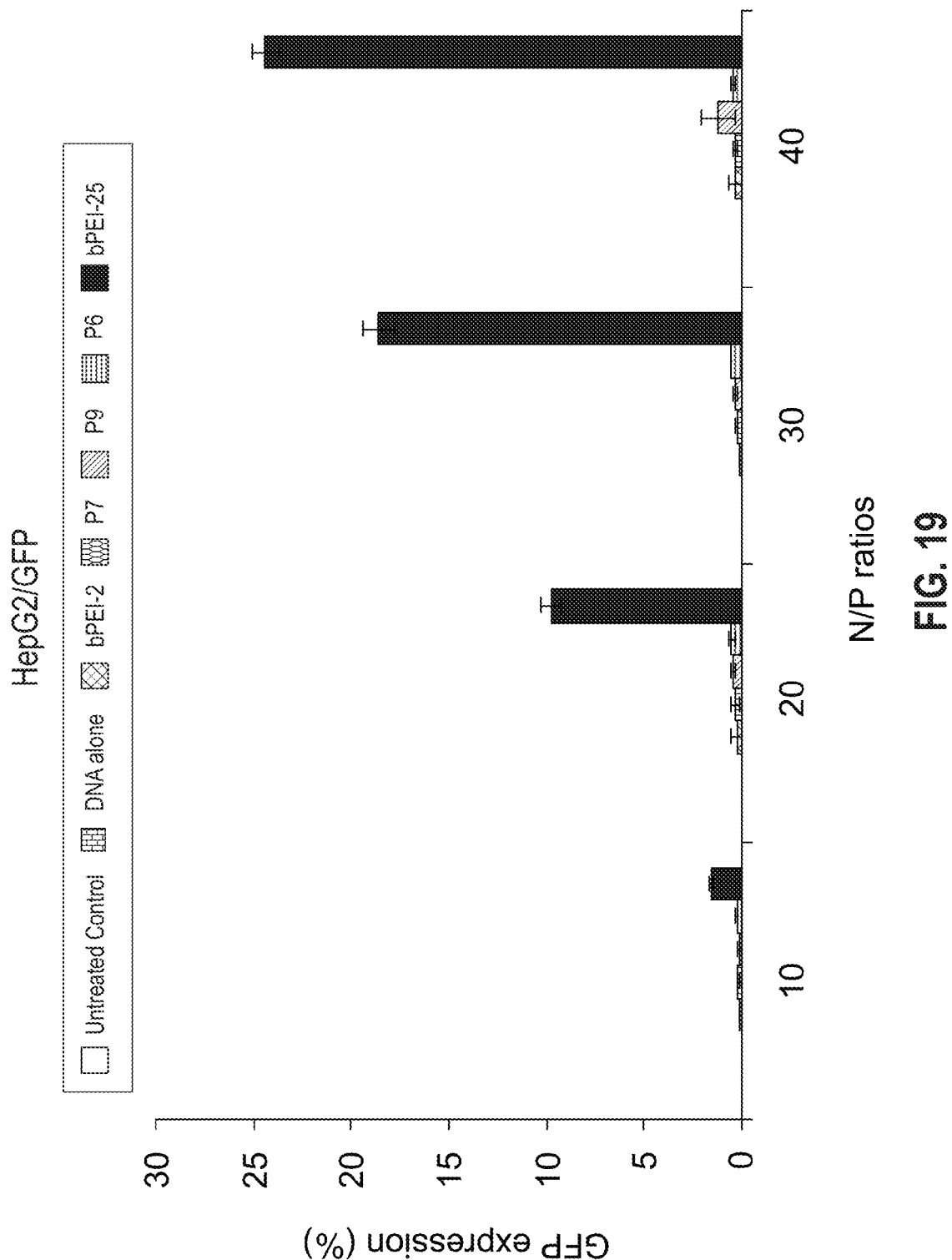
FIG. 19 is a bar graph comparing the in vitro GFP gene transfection efficiency in HepG2 cells of three modified bPEI-2 polymers P6, P7, and P9 at various N/P ratios.

FIG. 19 is a bar graph comparing the in vitro GFP gene transfection efficiency in HepG2 cells of three modified bPEI-2 polymers P6, P7, and P9 at various N/P ratios. Controls included untreated cells, GFP gene alone, non-modified bPEI-2, and non-modified bPEI-25. Non-modified bPEI-2, P6 and P7 had a peak efficiency of less than 1% at N/P 40, while non-modified bPEI-25 had a peak efficiency of about 24% at N/P 20. P9 had peak efficiency of about 1.5% at N/P 40.

SUMMARY

In some instances an average modification of one primary amine group of bPEI-2 was sufficient to increase the luciferase expression level about ten-fold in SK-OV-3 and HepG2 cells while maintaining low cytotoxicity. High transfection efficiency of the modified bPEI-2 polymers occurred when about 10% to about 40% of the primary amine groups of the non-modified bPEI-2 were modified. Cell viability of the modified bPEI polymers was greater than 80%. Cyclic carbonate monomers bearing a pendant ester having an aromatic ring and/or a urea group showed the highest gene expression levels.

The modified bPEI-2 polymers are robust gene transfection agents, capable of delivering to each of the tested cell types using a wide variety of modifying groups. Transfection efficiency was positively improved in both the HepG2 and SK-OV-3 cell lines.

Notably, improved transfection efficiency was obtained with modified bPEI-2 polymers having only a non-charged carbamate group. None of the modified bPEI polymers contained a quaternary amine.

The modified bPEI-2 polymers can also be used as delivery vehicles for proteins and/or drugs.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. When a range is used to express a possible value using two numerical limits X and Y (e.g., a concentration of X ppm to Y ppm), unless otherwise stated the value can be X, Y, or any number between X and Y.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:

1. A branched polyamine, comprising:
   about 8 to about 12 backbone tertiary amine groups, about 18 to about 24 backbone secondary amine groups, a positive number n' greater than 0 of backbone terminating primary amine groups, and a positive number q greater than 0 of backbone terminating carbamate groups of formula (2):

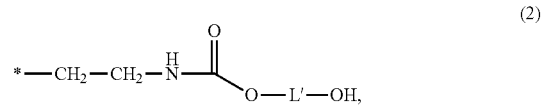

wherein:
   (n'+q) is a number equal to about 8 to about 12,
   the starred bond of formula (2) is linked to a backbone nitrogen of the branched polyamine,
   L' is a divalent linking group comprising 3 to 30 carbons, and
   q/(n'+q)×100% equals about 9% to about 40%.

2. The branched polyamine of claim 1, wherein the branched polyamine consists essentially of n' primary ethylenimine repeat units, about 18 to about 24 secondary ethylenimine repeat units, about 8 to about 12 tertiary ethylenimine repeat units, and q carbamate groups of formula (2).

3. The branched polyamine of claim 1, wherein the branched polyamine is a carbamate functionalized branched polyethylenimine having a number average molecular weight of about 1600 to about 5000.

4. The branched polyamine of claim 1, wherein a gene complex of the branched polyamine is non-cytotoxic at N/P 10 to N/P 50.

5. The branched polyamine of claim 1, wherein L' comprises a phenyl urea moiety.

6. The branched polyamine of claim 1, wherein q/(n'+q)×100% equals about 9% to about 25%.

7. The branched polyamine of claim 1, wherein q/(n'+q)×100% equals about 9% to about 12%.

8. The branched polyamine of claim 1, wherein the carbamate groups are not charged.

9. The branched polyamine of claim 1, wherein the branched polyamine has no quaternary amine groups.

10. A branched polyamine, comprising:
    about 8 to about 12 backbone tertiary amine groups, about 18 to about 24 backbone secondary amine groups, a positive number n' greater than 0 of backbone terminating primary amine groups, and a positive number q greater than 0 of backbone terminating carbamate groups of formula (4):

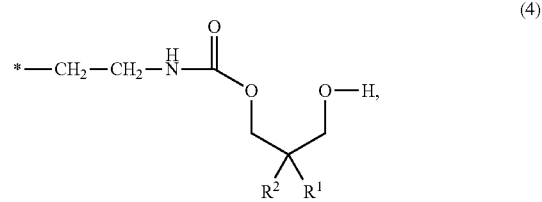

wherein
    the starred bond of formula (4) is linked to a backbone nitrogen of the branched polyamine,
    $R^1$ is hydrogen, methyl, or ethyl,
    $R^2$ is hydrogen or a monovalent radical comprising 1 to 27 carbons,
    (n'+q) is a number equal to about 8 to about 12, and
    q/(n'+q)×100% equals about 9% to about 40%.

11. The branched polyamine of claim 10, wherein $R^2$ is an ester *—C(=O)OR$^3$, wherein $R^3$ comprises 1 to 26 carbons.

12. A method, comprising:
    treating a branched first polymer comprising about 8 to about 12 primary amine groups, a plurality of secondary amine groups, and a plurality of tertiary amine groups with a cyclic carbonate monomer without polymerizing the cyclic carbonate monomer, thereby forming a branched polyamine comprising i) about 8 to about 12 backbone tertiary amine groups, ii) about 18 to about 24 backbone secondary amine groups, iii) a positive number n' greater than 0 of backbone terminating primary amine groups, and iv) a positive number q greater than 0 of backbone terminating carbamate groups of formula (2):

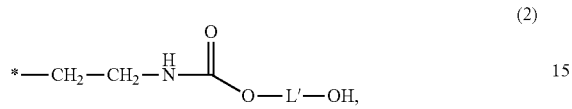

(2)

wherein:

(n'+q) is a number equal to about 8 to about 12, the starred bond of formula (2) is linked to a backbone nitrogen of the branched polyamine, L' is a divalent linking group comprising 3 to 30 carbons, and q/(n'+q)×100% equals about 9% to about 40%.

13. The method of claim 12, wherein the cyclic carbonate monomer comprises one or more protecting groups, and the method further comprises selectively removing the one or more protecting groups from the branched polyamine.

14. The method of claim 12, wherein the cyclic carbonate is a 6-membered ring cyclic carbonate.

15. The method of claim 12, wherein the branched first polymer is a branched polyethylenimine having a backbone consisting essentially of:

about 25 mol % primary ethylenimine repeat units having a structure

about 50 mol % secondary ethylenimine repeat units having a structure

about 25 mol % tertiary ethylenimine repeat units having a structure

wherein each starred bond represents an attachment point to another repeat unit of the backbone.

16. The method of claim 12, wherein the cyclic carbonate monomer is selected from the group consisting of

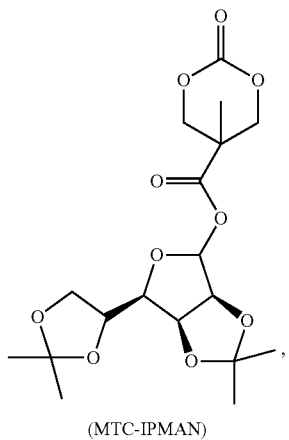
(MTC-IPMAN)

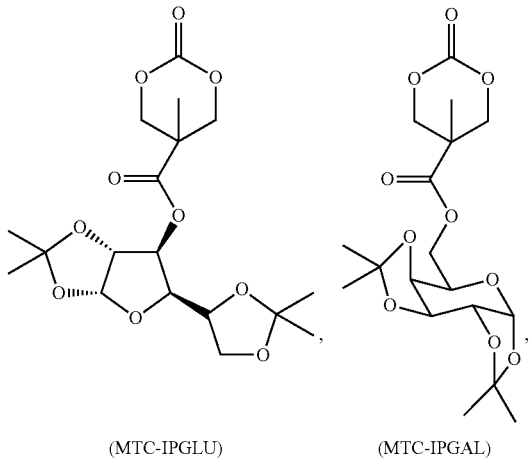
(MTC-IPGLU)  (MTC-IPGAL)

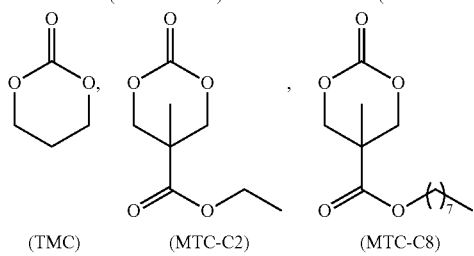
(TMC)  (MTC-C2)  (MTC-C8)

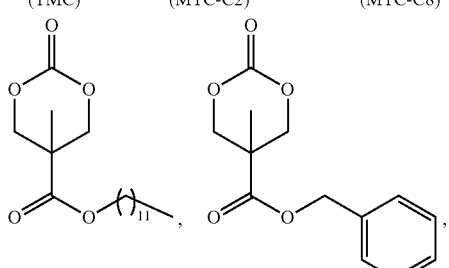
(MTC-C12)  (MTC-Bn)

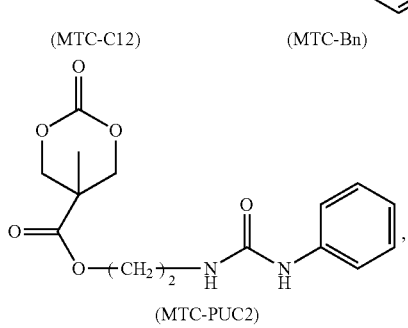
(MTC-PUC2)

-continued

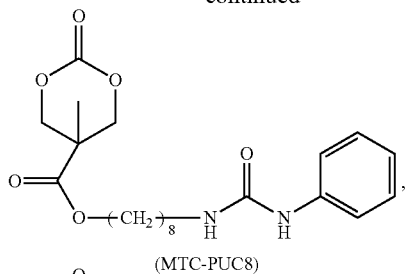

(MTC-PUC8)

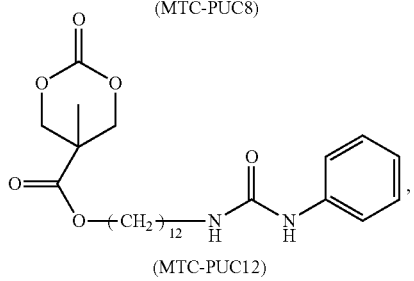

(MTC-PUC12)

and combinations thereof.

17. A complex, comprising:
a gene; and
a branched polyamine comprising about 8 to about 12 backbone tertiary amine groups, about 18 to about 24 backbone secondary amine groups, a positive number n' greater than 0 of backbone terminating primary amine groups, and a positive number q greater than 0 of backbone terminating carbamate groups of formula (2):

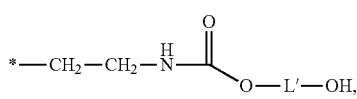
(2)

wherein:
(n'+q) is a number equal to about 8 to about 12,
the starred bond of formula (2) is linked to a backbone nitrogen of the branched polyamine,
L' is a divalent linking group comprising 3 to 30 carbons, and
q/(n'+q)×100% equals about 9% to about 40%.

18. A method of treating a cell, comprising contacting the cell with the complex of claim 17.

19. The method of claim 18, wherein the cell is a human tumor cell.

20. The method of claim 18, wherein the cell is a cancerous liver cell.

21. The method of claim 18, wherein the cell is a cancerous ovarian cell.

22. A branched polyamine having a structure according to formula (5):

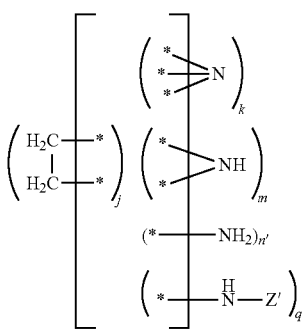
(5)

wherein j, k, m, n' and q represent molar amounts greater than 0, j has a value about 35 to about 47, k has a value of about 8 to about 12, m has a value of about 18 to about 24, (n'+q) has a value of about 8 to about 12, and q/(n'+q)×100% has a value of about 9% to about 40%, and each Z' is an independent moiety selected from the group consisting of

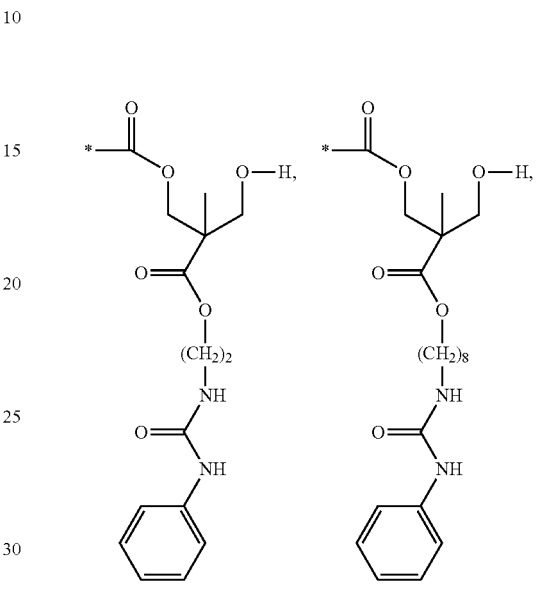

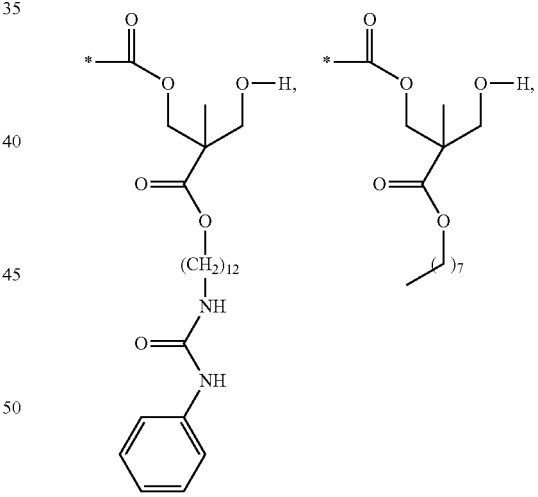

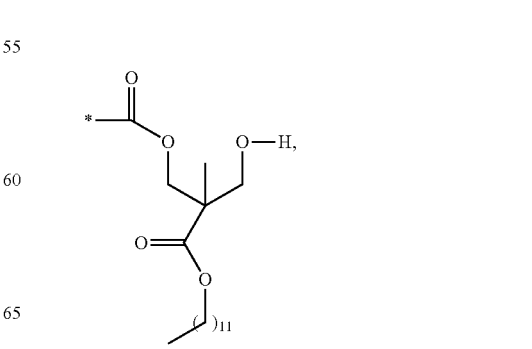

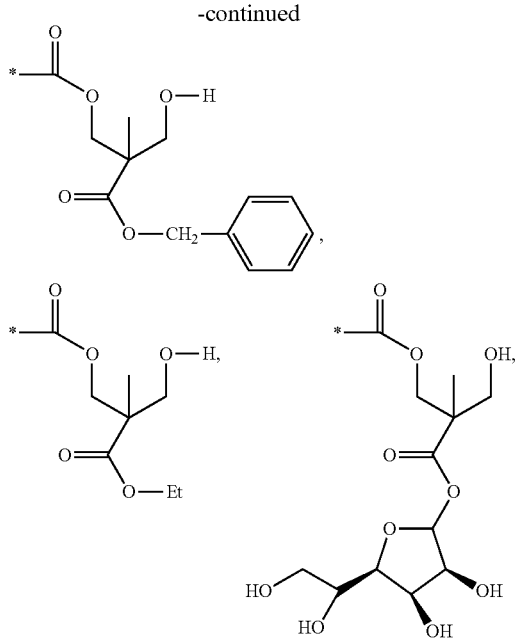
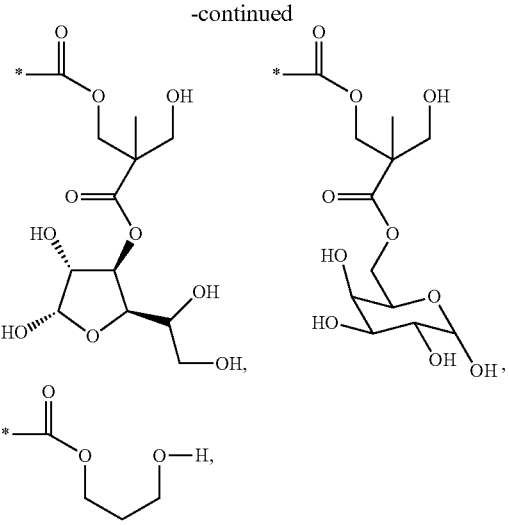
and combinations thereof.
* * * * *